United States Patent [19]

Buchanan

[11] Patent Number: 5,228,438
[45] Date of Patent: Jul. 20, 1993

[54] IMPLANTABLE PACEMAKER INCLUDING MEANS AND METHOD OF TERMINATING A PACEMAKER-MEDIATED TACHYCARDIA DURING RATE ADAPTIVE PACING

[75] Inventor: Stuart W. Buchanan, Saugus, Calif.

[73] Assignee: Siemens Pacesetter, Inc., Sylmar, Calif.

[21] Appl. No.: 772,822

[22] Filed: Oct. 8, 1991

[51] Int. Cl.$^5$ .............................................. A61N 1/368
[52] U.S. Cl. .............................................. 128/419 PG
[58] Field of Search ................................ 128/419 PG

[56] References Cited

U.S. PATENT DOCUMENTS

| | | | |
|---|---|---|---|
| 4,429,697 | 2/1984 | Nappholz | 128/419 PG |
| 4,452,248 | 6/1984 | Keller, Jr. | 128/419 PG |
| 4,485,818 | 12/1984 | Leckrone et al. | 128/419 PG |
| 4,493,325 | 1/1985 | Hartlaub et al. | 128/419 PG |
| 4,543,963 | 10/1985 | Gessman | 128/419 PG |
| 4,554,920 | 11/1985 | Baker, Jr. et al. | 128/419 PG |
| 4,554,921 | 11/1985 | Boute et al. | 128/419 PG |
| 4,572,192 | 2/1986 | Jackman et al. | 128/419 PG |
| 4,593,695 | 6/1986 | Wittkampf | 128/419 PG |
| 4,624,260 | 11/1986 | Baker, Jr. et al. | 128/419 PG |
| 4,686,989 | 8/1987 | Smyth et al. | 128/419 PG |
| 4,712,555 | 12/1987 | Thornander et al. | 128/419 PG |
| 4,712,556 | 12/1987 | Baker, Jr. | 128/419 PG |
| 4,714,079 | 12/1987 | Hedberg et al. | 128/419 PG |
| 4,781,194 | 11/1988 | Elmqvist | 128/419 PG |
| 4,788,980 | 12/1988 | Mann et al. | 128/419 PG |
| 4,802,483 | 2/1989 | Lindgren | 128/419 PG |
| 4,905,708 | 3/1990 | Davies | 128/419 PG |
| 4,920,965 | 5/1990 | Funke et al. | 128/419 PG |
| 4,944,298 | 7/1990 | Sholder | 128/419 PG |
| 4,969,465 | 11/1990 | Pless et al. | 128/419 PG |
| 5,002,052 | 3/1991 | Haluska | 128/419 PG |

OTHER PUBLICATIONS

Chorus 6003-6033 Implantable Dual-Chamber Pulse Generator DDD MO Physician's Manual, published by ELA Medical, Inc., Minnetonka, MN (19 ).

den Dulk, K., M.D. et al., "Merits of Various Anti--PCMT Features," Abstracts, 5th International Congress, Cardiostim 86 (Monaco, Jun. 19-21, 1986), *Clinical Progress in Electrophysiology and Pacing*, (Jun. 1986, vol. 4, Supplement) (Futura Publishing Company, Mt. Kisco, NY).

Primary Examiner—William E. Kamm
Attorney, Agent, or Firm—Malcolm J. Romano

[57] ABSTRACT

An atrial tracking dual-chamber pacemaker and method of use thereof for terminating a pacemaker-mediated tachycardia (PMT). The pacemaker includes means for determining whether the present heart rate exceeds a tachycardia reference rate, and if so, whether a PMT-indicating sequence of a tracked P-wave, including a retrograde P-wave followed by a V-pulse, occurs repetitiously for at least a predetermined number of cardiac cycles. The pacemaker includes means for measuring the interval between a P-wave and a V-pulse (PVI) and sets the PVI to 250 milliseconds when the measured value is less than 250 milliseconds. The pacemaker issues a PMT-terminating timed atrial pulse which is timed from a retrograde P-wave by a time equal to the PVI, plus a delay of about 25-100 milliseconds. In the event the atrial pulse fails to terminate the PMT, the process is repeated after a fixed number of cardiac cycles has occurred. An alternate embodiment includes determining a ventricular escape interval (VEI) which is equal to the AEI plus the PVI. Upon the delivery of the timed atrial pulse, the pacemaker changes to the VDD mode of operation, and immediately upon the occurrence of the following V-pulse which is a VEI displaced from the prior pulse, the pacemaker reverts to the DDD mode of operation.

42 Claims, 8 Drawing Sheets

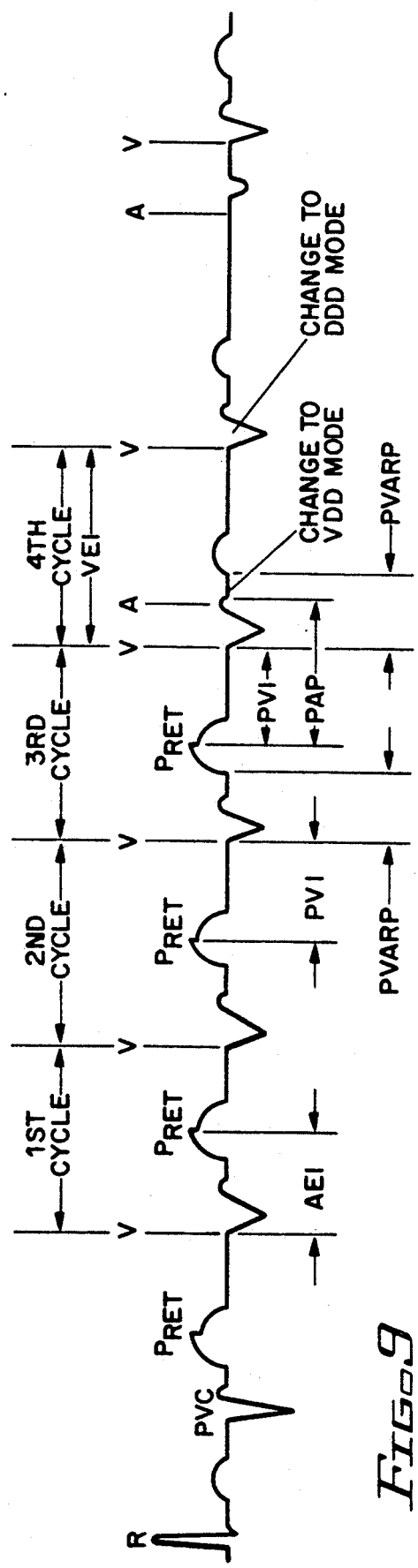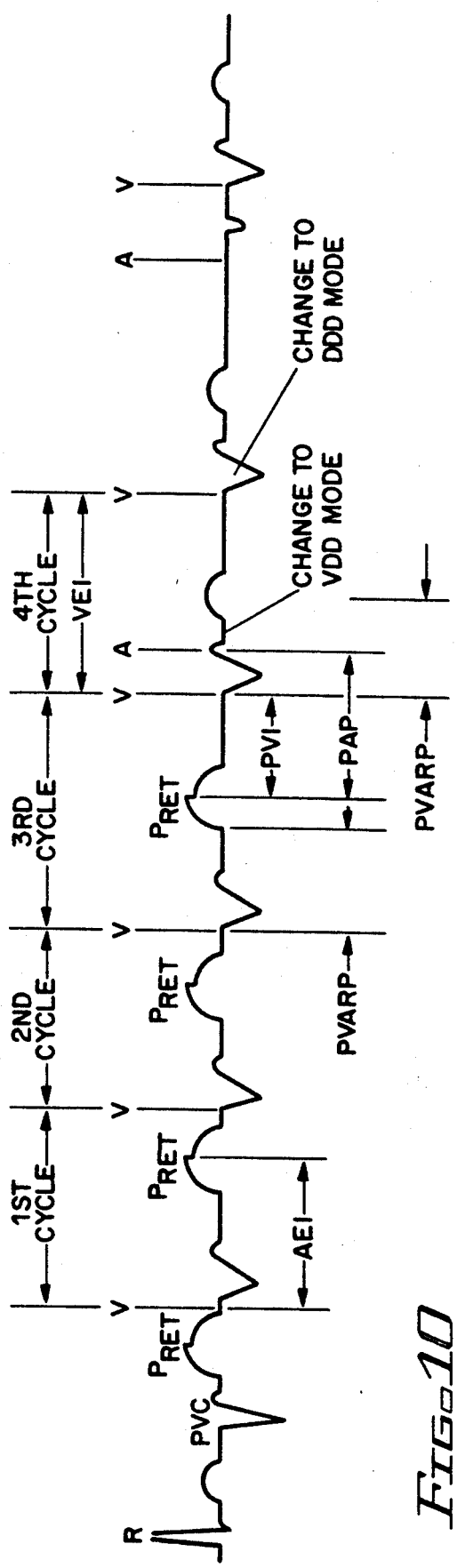

5,228,438

IMPLANTABLE PACEMAKER INCLUDING MEANS AND METHOD OF TERMINATING A PACEMAKER-MEDIATED TACHYCARDIA DURING RATE ADAPTIVE PACING

FIELD OF THE INVENTION

The present invention relates to cardiac pacemakers, and more particularly to implantable programmable dual-chamber cardiac pacemakers adapted to automatically detect and terminate the occurrence of a pacemaker-mediated tachycardia (PMT). Specifically, a pacemaker incorporating the present invention minimizes a slowdown in ventricular rate during activity or at rest when the PMT breaking algorithm is applied, such slowdown in ventricular rate being undesirable, especially during activity. Furthermore, the present invention terminates a PMT by an appropriately timed atrial pulse which is timed from the last retrograde P-wave, thus preventing atrial competition and causing an effective atrial stimulus and subsequent antegrade conduction thus preventing retrograde conduction from being detected by the pacemaker.

BACKGROUND OF THE INVENTION

In order to efficiently perform its function of a pump, the heart must maintain a natural A-V synchrony. The term "A-V synchrony" relates to the sequential timing relationship that exists between the contractions of the atria and the ventricles. In a given heart cycle or beat, the atria (A) contract prior to the ventricles (V) in accordance with a prescribed timing or synchronized relationship, hence the term "A-V synchrony." These contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram (ECG) and include a P-wave, representing the depolarization of the atria; the QRS-wave (sometimes referred to as a R-wave, the predominant wave of the group), representing the depolarization of the ventricles; and the T-wave, representing the repolarization of the ventricles. (It is noted that the atria also are repolarized, but this atrial repolarization occurs at approximately the same time as the depolarization of the ventricles; and any electrical signal generated by atrial repolarization is generally minute and masked out by the much larger QRS-wave on the ECG.)

Thus, it is the P-QRS-T cycle of waves that represent the natural A-V synchrony of the heart. These waves, including the timing relationships that exist therebetween, are carefully studied and monitored through conventional ECG techniques whenever the operation and performance of the heart is being examined.

A pacemaker is a medical device that assists the heart in maintaining a desired A-V synchrony by monitoring the atria and/or ventricles for the occurrence of P-waves and/or R-waves, and by producing stimulation pulses that are delivered to an appropriate chamber of the heart to cause that chamber to depolarize, and hence contract. (Because the main function of the pacemaker is to provide such stimulation pulses, a pacemaker is frequently referred to as a "pulse generator.") If, for some reason, the heart is unable to maintain its natural A-V synchrony, a pacemaker is utilized to monitor the heart and to provide electrical stimulation pulses when it senses that the heart is not maintaining proper A-V synchrony. A dual-chamber pacemaker, for example, monitors both the right atrium and right ventricle. If it senses an atrial depolarization at appropriate times, no atrial stimulation pulse is generated. If it senses a ventricular depolarization within a prescribed time after the atrial depolarization, no ventricular stimulation pulse is generated. If however, it fails to sense either the atrial or ventricular depolarization within prescribed time periods, then stimulation pulses, frequently referred to as an A-pulse (if delivered to the atrium) and/or a V-pulse (if delivered to the ventricle), are generated and delivered to the appropriate chamber of the heart at an appropriate time in order to maintain the correct heart rhythm.

One of the problems that complicates the operation of a dual-chamber pacemaker, i.e., one that is capable of sensing and/or pacing in both chambers of the heart, is "retrograde conduction." Retrograde conduction is a condition when the depolarization of the ventricles propagates *backwards* into the atria, causing the atria to depolarize prematurely. This atrial depolarization is manifest by the occurrence of a P-wave, frequently referred to as a "retrograde P-wave". A retrograde P-wave appears on the ECG substantially the same as a natural P-wave except that it occurs much too soon after a ventricular contraction. (A "natural" P-wave results from the natural A-V synchrony of the heart as set by the heart's natural sinus rhythm, and is hereafter referred to as a "sinus" P-wave.) See U.S. Pat. No. 4,788,980 for a more thorough description of retrograde conduction.

Unfortunately, the pacemaker sensing circuits cannot readily distinguish between a retrograde P-wave and a sinus P-wave. A significant problem thus exists because once a P-wave is sensed, the pacemaker (depending upon its mode of operation) will typically generate a V-pulse a prescribed delay thereafter, referred to herein as the "P-V delay," unless an R-wave is sensed during the P-V delay. (It is noted that much of the literature refers to the P-V delay, as that term is used herein, as the "A-V delay," or AVD. Further, some pacemakers employ one delay, a P-V delay, following a P-wave, and another slightly different delay, or AV delay, following an A-pulse. For purposes of the present invention, all such delays following an atrial event, whether an A-pulse or P-wave, are referred to herein as the "P-V delay.") If the sensed P-wave is a retrograde P-wave, an R-wave will not likely occur during this relatively short P-V delay time interval because the contraction of the ventricles just occurred prior to the retrograde P-wave. Thus, at the conclusion of the P-V delay, a V-pulse is generated by the pacemaker, causing the ventricles to again contract, which contraction causes another retrograde P-wave. This retrograde P-wave, in turn, causes another V-pulse to be generated after the P-V delay, causing the cycle to repeat, resulting in a pacemaker mediated tachycardia, or PMT. (A "tachycardia" is a very rapid rhythm or rate of the heart.)

Note that during a PMT, it is the pacemaker itself that causes or "mediates" the tachycardia by tracking each P-wave caused by the retrograde conduction, and providing a ventricular stimulation pulse a programmed P-V delay thereafter. The pacemaker thus provides the forward conduction path (from the atria to the ventricles) electronically by tracking each P-wave and generating a V-pulse (ventricular stimulation pulse) if no R-wave is sensed within a prescribed time thereafter (the programmed P-V delay). The reverse or backward conduction path (from the ventricles to the atria) is provided by retrograde conduction originating with the depolarization of the ventricles, which depolarization occurs as a result of the V-pulse. Thus, retrograde conduction passes the ventricular depolarization back to the atria, causing the atria to depolarize (resulting in a retrograde P-wave), and the process repeats.

Unfortunately, a PMT can be triggered by numerous events. The most common mechanism for triggering a PMT is a premature ventricular contraction, or PVC. A PVC, in turn, is not an uncommon occurrence for most mammalian hearts. A cough or a sneeze, for example, may cause a PVC. Unfortunately, for a patient having a dual-chamber pacemaker that is set to operate in a mode that tracks P-waves and stimulates the ventricle, the occurrence of a single PVC can reset the pacemaker timing in a manner that allows the pacemaker to begin tracking retrograde P-waves, causing a PMT to occur. Such PMT, if allowed to continue for more than just a few cycles, seriously impacts the ability of the heart to efficiently perform its function of a pump. What is needed, therefore, is a system or method for accurately detecting the occurrence of a PMT and quickly terminating such PMT once detected.

One common technique used to prevent a PMT is to first detect a PVC, and assume that any rapid heart rate thereafter is a PMT. Thus, in order to prevent the occurrence of a PMT, it is known in the art for a pacemaker, upon the detection of a PVC, to revert to a DVI mode of operation for one cycle. (For an explanation of the various pacemaker modes—DDD, DDI, DVI, VVI, etc.—see, e.g., U.S. Pat. No. 4,712,555.) This response, in effect, turns off the atrial sense amplifiers for one cycle. Hence, subsequent to the detection of the PVC, no P-waves can be sensed by the pacemaker because the electronic sense circuits are masked from sensing any atrial events, whether a retrograde event or a normal event. It is thus not possible for the pacemaker to generate a V-pulse one P-V delay after a retrograde P-wave, because the retrograde P-wave is not sensed. If the retrograde P-wave is not sensed, the occurrence of a PMT is prevented.

One problem with this approach of turning off the atrial sense amplifiers for the one cycle is that if during the one cycle response using the DVI mode a normal sinus rhythm with spontaneous R-wave occurs, the PVC response remains on because the pacemaker interprets the spontaneous R-wave as another PVC. Thus, even though a possible PMT is prevented, the loss of normal P-wave tracking may occur because P-waves are masked by the response to the detected PVC, and any R-waves that are detected are interpreted as another PVC. Hence, the PVC response may become "stuck," as there is no way for it to terminate. Loss of P-wave tracking may occur from seconds to hours depending on the pacemaker's programmed rate settings and the patient's sinus rate.

Another technique known in the art aimed at preventing a PVC from triggering a PMT, is to extend the Post Ventricular Atrial Refractory Period (PVARP) by a prescribed amount, such as 480 milliseconds, upon the detection of a PVC, thus masking retrograde conduction during this period of time. In addition, the atrial escape interval (V-A delay) is fixed to a prescribed value, such as 830 milliseconds, regardless of the programmed or sensor indicated rate (if a sensor is used, such as is the case in a rate-responsive pacemaker). See, e.g., U.S. Pat. No. 4,788,980. The difference between the selected PVARP value and the fixed VA delay, which difference is 350 milliseconds for the example given, advantageously allows a "window of time" during which a P-wave may be detected.

The extended PVARP approach described above is an improvement over the DVI on PVC approach because the extended PVARP interval is sufficient to mask most retrograde conduction in the majority of patients, and P-waves not related to retrograde conduction can still be tracked. However, unless the sinus P-wave or other atrial event (e.g., an A-pulse) occurs during the window of time defined subsequent to the extended PVARP interval and prior to the termination of the VA delay (e.g., during the 350 milliseconds time period for the example times given above), the PVC response continues. Unfortunately, the PVC response can continue if P-waves fall within the extended PVARP interval (which will not be detected) followed by R-waves that cause the VA delay interval to be reset (with the R-waves being interpreted as PVCs). When this occurs, the PVC response thus causes a fixed atrial escape interval. In turn, this results in a slowdown of ventricular rate because the rate of pacing is made up of the A-V delay (P-V delay) and the atrial escape interval (V-A delay). Such a reduced ventricular rate may not meet the patient's then-existing physiological needs. What is needed, therefore, is a system that in its attempt to prevent a PMT does not slow down the patient's ventricular rate for a prolonged period.

Another technique known in the art for recognizing and breaking a PMT is used by the SYNCHRONY® pacemaker, manufactured by Siemens-Pacesetter, Inc., Sylmar, Calif. The SYNCHRONY® pacemaker utilizes both a maximum tracking rate (MTR) and a tachycardia recognition rate (TRR). The TRR is less than or equal to the MTR. Whenever the SYNCHRONY® pacemaker is pacing in the ventricle as a result of tracking P-waves and senses a rate that is higher than the TRR, the tachycardia termination routine is activated. This tachycardia termination routine operates as follows: following the 10th–127th beat at a heart rate greater than the TRR, the PVARP is extended to approximately 500 milliseconds. This is a sufficient extension to prevent most retrograde P-waves from being sensed, since most retrograde P-waves occur within 250–400 milliseconds after the contraction of the ventricle. Following the 500-millisecond PVARP, there is an approximately 350-millisecond alert period during which the pacemaker is able to sense a sinus P-wave. If no P-wave occurs by the end of this 350-millisecond alert period, the pacemaker logic circuits cause an atrial stimulation pulse, or A-pulse, to be generated. In either event (i.e., whether a P-wave is sensed or an A-pulse is generated), this should be the end of the PMT. This method of terminating a PMT is described more thoroughly in U.S. patent application Ser. No. 07/491,385, filed 03/09/90, which application is assigned to the same assignee as is the present application, and which application is incorporated herein by reference.

Unfortunately, while the PMT termination approach described above operates to terminate most PMT's, there are some situations where this is not the case. For example, if a ventricular beat (R-wave) is sensed before the sensed sinus P-wave or the delivered A-pulse, the pacemaker logic causes PVARP to remain extended for another cardiac cycle, thereby rendering the pacemaker incapable of sensing P-waves for an additional 500 millisecond period. This extended PVARP of 500 milliseconds continues for each cardiac cycle where an R-wave is sensed before a P-wave. Thus, as R-waves continue to be sensed, it is possible for PVARP to be continually extended, thereby effectively eliminating any capability of the pacemaker to sense and track P-waves (because P-waves cannot be sensed during the 500 milliseconds after a ventricular contraction). What is needed, therefore, is an improved response to a sensed PMT that is not extended indefinitely.

An additional problem is created whenever PVARP is extended when the pacemaker is a rate-responsive pacemaker. In a rate-responsive pacemaker, the pacing rate is controlled by a separate activity sensor that detects patient activity (or some other parameter indicative of the need to adjust the heart rate). If such an activity sensor is employed, and if the extended PVARP response continuously repeats (i.e., R-waves are sensed but P-waves are not), then, in effect, the activity sensor is disabled. For example, if the P-V delay is 150 milliseconds, then the rate during an extended PVARP response would be, using the same numbers presented above, 150 milliseconds + 850 milliseconds = 1000 milliseconds, or about 60 beats per minute. Any sinus P-waves falling within the extended PVARP interval are not sensed, hence the extended PVARP response remains on when accompanied by detected R-waves prior to the end of the V-A delay. Thus, sensor controlled rates are prevented from being effective since the extended PVARP interval controls the atrial escape interval. In other words, since the extended PVARP response slows down the ventricular rate from a higher sensor controlled rate, it is more likely that a sinus rhythm will keep the extended PVARP response on, thereby causing a slower ventricular rate, which slower rate may be undesirable when the patient may be in need of increased cardiac output during activity. Hence, multiple extensions of PVARP upon the detection of a PMT may be an inappropriate response for a sensor-driven rate responsive pacer. What is needed, rather, is a technique or method for clearly recognizing and responding to the occurrence of a PMT, regardless of whether the pacemaker responsible for the PMT is a rate-responsive pacemaker or a fixed (programmable) rate pacemaker.

It is thus evident that there is a need in the art for a system that can terminate a PMT during periods of activity, which PMT response will reduce ventricular rate slowdown during the PMT response, and thus prevent an abrupt change in cardiac output, and allow for P-wave tracking immediately after the PVARP interval. What is further needed is a method of PVARP programming that will allow tracking P-waves at higher rates such as during periods of activity. Programming PVARP long (such as 480 milliseconds during the PMT response, as previously described) will defeat the purpose of tracking P-waves at higher rates and will cause a slowdown in the ventricular rate, as previously described. With an appropriately timed atrial pulse, which pulse is timed from the last P-wave, the PVARP interval does not have to be programmed long as in prior art since the atrial pulse antegrade conduction and P-wave retrograde conduction will extinguish each other and prevent sensing retrograde conduction, which might otherwise be sensed after a PVARP interval which was not extended. The present invention advantageously addresses the above and other needs.

SUMMARY OF THE INVENTION

The present invention is embodied in a system for terminating pacemaker-induced tachycardia. Broadly stated, upon detection of a PMT and upon satisfaction of several heart rate and timing criteria, a timed atrial pulse is delivered to the atrium of the heart. The atrial pulse is timed uniquely from a detected retrograde P-wave to terminate the PMT.

The system includes a pacemaker capable of VDD and DDD pacing. These modes of operation, in part, are implemented in rate-responsive pacemakers, in which the system is preferably used. The system includes means for detecting the occurrence of V-pulses and P-waves, which P-waves include retrograde P-waves in a prescribed sequence of cardiac cycles. The sequence comprises a P-wave followed by a V-pulse, and the time interval therebetween is defined as the P-V interval (PVI), and the time interval between successive V-pulses is defined as the V-V interval (VVI).

The system further includes a stimulation means which is responsive to the detection means and issues a timed atrial pulse. The atrial pulse as noted, is timed from a P-wave, preferably a retrograde P-wave. The time to the timed atrial pulse comprises a predetermined delay made up of the PVI plus a delay interval. The delay interval is in the range of about 25-100 milliseconds, insuring that there will be no competition between the timed atrial pulse and a naturally occurring atrial pulse.

The pacemaker is adjusted to pace in the VDD mode at least after the occurrence of a timed atrial pulse. The pacemaker is then adjusted to pace in the DDD mode upon the occurrence of a V-pulse immediately subsequent to the timed atrial pulse.

In a preferred embodiment, the prescribed sequence of cardiac cycles includes at least four cycles comprising a first, a second, a third and a fourth cycle. The four cycles occurring successively wherein the detection means detects the value of the V-V interval in the first and second cycles and detects the value of the PVI in the second cycle. Further, the stimulation means times the timed atrial pulse from a retrograde P-wave detected in the third cycle and wherein the time to the atrial pulse comprises the PVI plus a delay interval, the delay interval being in the range of about 25-100 milliseconds, such that the timed atrial pulse occurs in the fourth cycle.

The invention described herein further contemplates a method of terminating a pacemaker-mediated tachycardia based upon the use of a timed atrial pulse, the pulse being timed from a retrograde P-wave. The method includes the steps of sensing a V-pulse, which is followed by a P-wave, in a plurality of successive cardiac cycles to detect an atrial escape interval. A P-V interval is sensed by detecting a P-wave which is followed by a V-pulse in the plurality of successive cardiac cycles. Successive V-pulses are sensed to determine a V-V interval, wherein the interval comprises the elapsed time between successive V-pulses. Heart rate is monitored to determine whether the rate is in excess of a tachycardia reference rate. If the heart rate exceeds the tachycardia reference rate, the sequence of P-waves followed by V-pulses is sensed to see whether the sequence continues repetitiously for a predetermined number of sequences. The atrium is then stimulated with a timed atrial pulse when the number of V-V intervals exceeds a predetermined number and the heart rate exceeds the tachycardia reference rate, concurrently with the P-V sequence continuing repetitiously and the P-V interval being less than a predetermined value.

The atrial pulse is timed from a P-wave, a predetermined delay, such that the delay comprises the P-V interval, plus a delay interval, which is in the range of about 25-100 milliseconds. Preferably, the atrial pulse is timed from a retrograde P-wave. Preferably, the predetermined number of V-V intervals is in the range of about 2-20. Preferably, the method further comprises commencing a VDD mode of operation immediately after the timed atrial pulse is delivered, and commencing a DDD mode of operation upon the occurrence of a V-pulse which follows immediately from the timed atrial pulse.

BRIEF DESCRIPTION OF THE DRAWINGS

The above and other aspects, features and advantages of the present invention will be more apparent from the following more particular description thereof, presented in conjunction with the following drawings wherein:

FIG. 9 is a composite timing diagram showing operation of the method depicted in FIG. 8 to terminate a PMT at the maximum tracking rate; and FIG. 10 is a composite timing diagram showing operation of the method depicted in FIG. 8 to terminate a PMT when the PMT is below the maximum tracking rate.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In order to better understand the present invention, it will first be helpful to review some basic cardiac physiology, and the manner by which a pacemaker assists a mammalian heart in maintaining a desired A-V synchrony. Accordingly, reference is made to FIG. 1, where there is shown a typical ECG-type waveform illustrating a normal cardiac cycle of a heart. Such waveforms may be obtained using conventional skin-electrode ECG techniques. Alternatively, intracardiac ECG features of modern pacemakers provide similar ECG information through the use of the telemetry features of such pacemakers.

Figure 1:
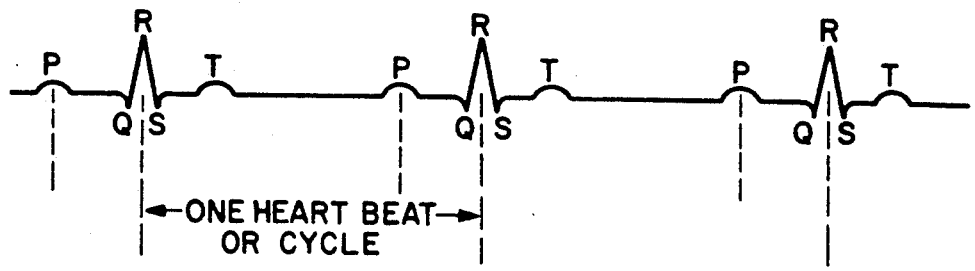
FIG. 1 is a typical ECG-type waveform illustrating the normal A-V synchrony of the heart.

Beginning at the left of the waveform of FIG. 1, there is shown a P-wave. This P-wave represents the electrical activity coincident with the depolarization of the atria of the heart. Depolarization of the atria is accompanied by contraction of the atria, thereby allowing blood to be pushed from the atria into the ventricles of the heart. While those skilled in the art will recognize that depolarization and contraction are not necessarily simultaneous events, they will be assumed to be simultaneous events for purposes of this patent application, and the terms "depolarization" and/or "contraction" are meant to be synonymous.

A short time subsequent to the generation of the P-wave, the QRS complex appears, representing the depolarization of the ventricles. The time period between the P-wave and the QRS-wave (often referred to as simply an R-wave) is an important time interval in the operation of the heart because it represents the time needed for the blood to flow from the atria into the ventricles. The R-wave is followed by a T-wave, which wave represents the electrical activity associated with the depolarization of the ventricles.

As known to those skilled in the art, the ventricles do most of the work in pumping the blood throughout the body. Typically, one heart beat or heart cycle is measured as the time interval between succeeding R-waves, simply because the R-wave typically represents the easiest of the waves to identify and measure. A heart beat may, of course, be measured relative to any point within the heart cycle, such as between succeeding T-waves or P-waves.

A certain rhythm or synchrony must occur if the heart is to perform its function of a pump efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricles. If the depolarization of the atria or ventricles do not occur naturally, then a pacemaker may be employed to provide stimulation pulses to these respective heart chambers in order to trigger the required depolarization/contraction at the appropriate time periods of the heart cycle.

Figure 2:
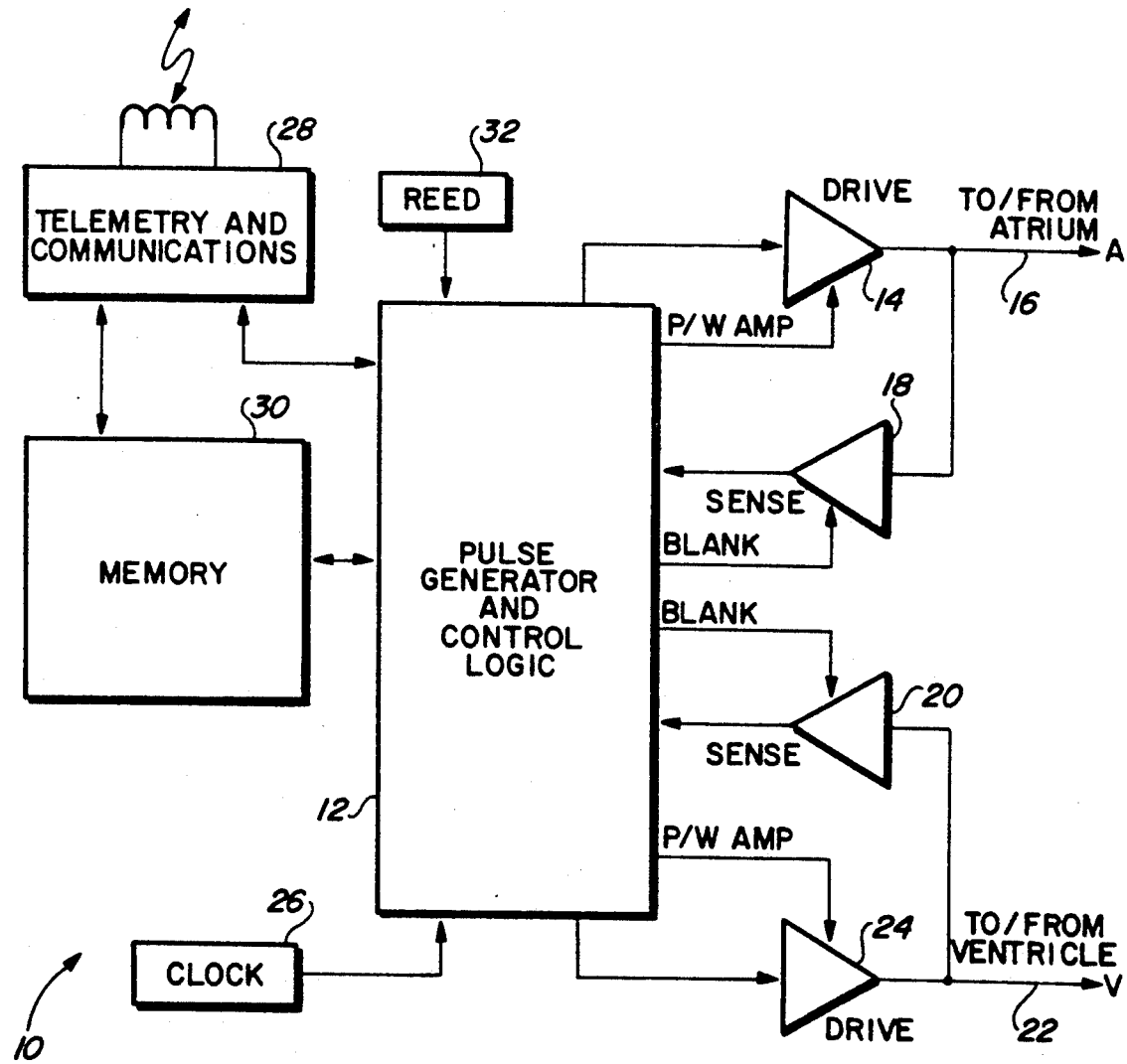
FIG. 2 is a block diagram of an implantable, programmable, dual-chamber pacemaker.

Referring next to FIG. 2, a block diagram of a typical atrial tracking dual-chamber pacemaker 10 is illustrated. As explained below, the circuitry shown in FIG. 2 may be used to carry out the PMT termination method of the present invention. In FIG. 2, Pulse Generator and Control Logic 12 generates the appropriate timing signals and sequences to enable stimulation pulses to be generated and delivered to the heart. Stimulation pulses are delivered to the right atrium of a heart (not shown) through an atrial drive amplifier 14 and an atrial lead or conductor 16. This same atrial lead 16 is connected to an atrial sense amplifier 18. This sense amplifier 18 monitors the electrical activity of the atrium to determine if a sinus P-wave, representing the natural depolarization of the atrium, has occurred. If such sinus atrial activity is sensed, then Pulse Generator and Control Logic 12 inhibits the stimulation pulse provided to the drive amplifier 14 and provides for a ventricular stimulus after a predetermined time period (referred to as the P-V delay). However, if a sinus P-wave has not been sensed after a prescribed period of time, typically referred to as the atrial escape interval, then the Pulse Generator and Control Logic 12 delivers a stimulation pulse ("A-pulse") through the drive amplifier 14 to the atrium over lead 16. The pulse width and amplitude of this stimulation pulse are controlled by the Pulse Generator and Control Logic 12.

In a similar manner, the Pulse Generator and Control Logic 12 senses the electrical activity occurring in the right ventricle of the heart through a sense amplifier 20 connected to a ventricular lead 22. If naturally occurring ventricular electrical activity is not sensed within an appropriate ventricular escape interval, then the Pulse Generator and Control Logic 12 generates a ventricular stimulation pulse ("V-pulse") of a prescribed pulse width and amplitude, delivered through the drive amplifier 24, in order to cause the desired ventricular contraction. If naturally occurring ventricular electrical activity is sensed, i.e., if an R-wave is sensed, then the Pulse Generator and Control Logic 12 inhibits the pulse provided to the drive amplifier 24 and resets the pacemaker timing logic within the Pulse Generator and Control Logic 12.

Clock circuitry 26 provides the basic clock signals or timing signals from which the Pulse Generator and Control Logic 12 operates. Telemetry and communications circuitry 28 provides a means whereby information can be telemetered to and from the implanted pacemaker. Control information that varies the basic escape intervals of the pacemaker, for example, may be received through the telemetry and communications circuitry 28 and stored in a memory 30, as may control information that sets the desired pulse width and/or amplitude of the stimulating pulse, as well as other control parameters used within the pacemaker. Such control information may also be passed directly to the Pulse Generator and Control Logic 12, if desired. Similarly, electrical activity of the heart, as sensed through the sense amplifiers 18 and 20, can be telemetered external to the pacemaker through the telemetry and communications circuitry 28, thereby allowing an attending physician or other medical personnel, e.g., cardiologist, to monitor the activity of the heart without the use of external skin electrodes.

A magnetic reed switch 32 is also typically employed with implanted pacemakers in order to control the programmable functions of the device. With a suitable programming apparatus in place, the reed switch 32 is closed and the attending physician or cardiologist can effectuate any desired changes in the operation of the pacemaker by sending appropriate control signals and commands over the telemetry and communications circuitry 28. Without the appropriate programming apparatus, the reed switch 32 remains open, and the telemetry and communications circuitry 28 is not operable.

Figure 3A:
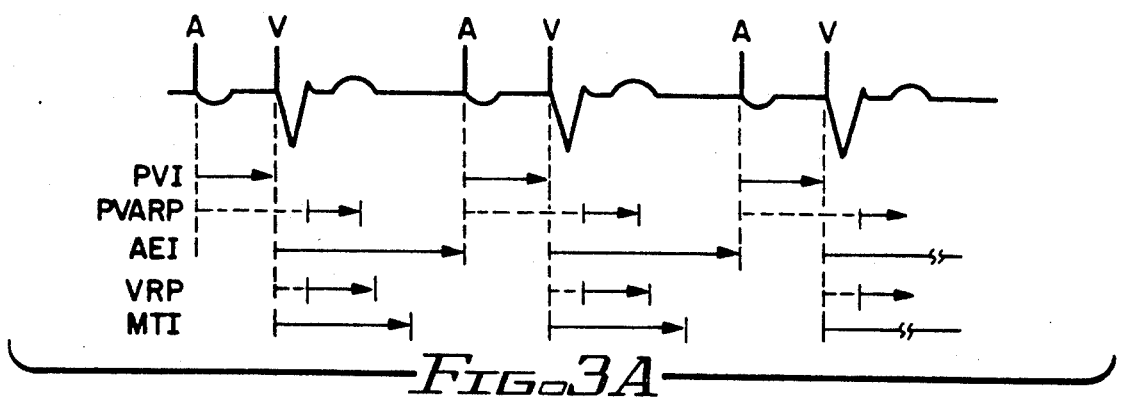
FIG. 3A is a composite timing diagram illustrating how the A-V synchrony of the heart is maintained when both atrial and ventricular stimulation pulses are provided to the heart by a dual-chamber pacemaker.

Referring next to FIG. 3A, a composite timing diagram illustrating the operation of a typical demand-type, dual-chamber pacemaker, is illustrated. In this and other timing diagrams used herein, the stimulation pulses generated by the pacemaker are illustrated as a narrow spike labeled with either an A (for an atrial stimulation pulse) or a V (for a ventricular stimulation pulse). Further, unless otherwise indicated, the response of the heart to an applied stimulation pulse is indicated in the figures as having an opposite polarity from that shown in FIG. 1. (FIG. 1 depicts the natural or sinus rhythm of the heart, and thus the heart responds without the application of a stimulation pulse.) This is done to clearly distinguish in the figures naturally occurring events of the heart from pacemaker-induced (paced) events.

Included in the timing diagram of FIG. 3A are representations of the various timing intervals that are generated by the control logic 12 (FIG. 2). Many of these time intervals are programmable, meaning that the length of such intervals can be varied by sending appropriate control signals over the telemetry and communications circuitry 28 to the memory circuits 30 of FIG. 2. As known to those skilled in the electronic arts, there are numerous methods and techniques through which a time interval can be varied. One such technique involves loading an appropriate data word into a prescribed memory location, which data word is subsequently loaded into an appropriate counter of the control logic 12. A basic clock signal is then used to clock this counter until the desired count is reached, at which time a terminal count signal (frequently termed a "timed-out" signal) is generated to indicate the end of the desired time interval. By merely changing the value of the data word that is loaded into memory, and knowing or controlling the rate of the clock signal, the length of the time interval can be varied or programmed to a desired value. Analog techniques may also be used to generate a time interval, such as are used within commercially available, or equivalent, one-shot multivibrator circuits.

The time intervals shown in the timing diagrams that follow are indicated by a horizontal line. If the time interval has "timed-out"—that is, if it has reached its terminal count—an arrowhead is placed on the horizontal line, pointing to the point in time at which the time interval terminates. (The horizontal axis of the timing diagrams represents the time axis.) It is noted that the timing drawings are not necessarily drawn to scale, nor with linear horizontal or vertical axes. It is also noted that some cardiac events, such as the T-wave, may be omitted from some of the timing diagrams. If a sensed electrical event occurs prior to the termination of a given interval, which event inhibits the generation of a stimulation pulse (or alters some other operation of the pacemaker) then a dot is placed on the horizontal line indicating the point in time at which the sensed event terminates or resets that particular interval.

Shown in FIG. 3A are five basic time intervals. These five time intervals are not the only time intervals defined by the Control Logic 12 and used in the operation of a pacemaker, but are some of the most pertinent time intervals utilized by the present invention. These five intervals are: (1) the P-V interval, or PVI, representing the desired time interval between atrial depolarization and ventricular depolarization; (2) the post ventricular atrial refractory period, or PVARP, representing the time interval subsequent to a ventricular event during which the atrial sensing circuits are disabled; (3) the atrial escape interval, or AEI, representing the time interval after which, in the absence of naturally occurring atrial activity during such interval, an A-pulse is generated and delivered to the atrium (sometimes also referred to as the V-A interval) or in the case of VDD mode, the ventricular escape interval (VEI), where in the absence of atrial activity or ventricular activity, a ventricular pulse (V-pulse) will be delivered; (4) the ventricular refractory period, or VRP, representing the interval during which the ventricular sense amplifier 20 (FIG. 2) is disabled; and (5) the maximum tracking interval, or MTI, representing the interval that defines the maximum tracking rate at which the pacemaker may operate. (The intervals MTI +PVI thus define the shortest possible time period of a pacemaker-defined cardiac cycle, and hence, the maximum possible paced ventricular rate.)

With the above basic timing intervals thus defined, the following description of FIGS. 3A-3E will be presented. As indicated previously, FIG. 3A illustrates how a pacemaker is used to maintain a desired rhythm or synchrony of the heart. For the situation shown in FIG. 3A, it is assumed that the heart cannot provide its own atrial or ventricular contractions at a suitable rate, and that the pacemaker must therefore provide the stimulation pulses required to maintain the desired heart rate. Accordingly, an atrial stimulation pulse, A, is provided in order to invoke a contraction of the atria. This event triggers the P-V interval, PVI. At the termination of the PVI, a ventricular stimulation pulse, V, is generated and applied to the heart. This stimulation pulse causes the ventricles to contract, as indicated by the inverted R-wave. The generation of the ventricular stimulation pulse, or V-pulse, also triggers the beginning of the post ventricular atrial refractory period, or PVARP; the atrial escape interval, or AEI; the ventricular refractory period, or VRP; and the maximum tracking interval, or MTI. At the conclusion of the AEI (or V-A interval), there having been no P-waves sensed, another A-pulse is generated in order to produce a contraction of the atria, thereby initiating the next cycle of the heart. Thus, the events previously described begin again and the cycle repeats itself, with a V-pulse being generated after the PVI subsequent to the A-pulse, and an A-pulse being generated after the AEI subsequent to the V-pulse. In this manner, the desired rhythm or synchrony of the heart is maintained as controlled by the programmable PVI and AEI intervals. It is noted that during the refractory periods PVARP and VRP, no cardiac activity can be sensed from the respective heart chambers. Thus, during PVARP, no atrial activity can be sensed. Similarly, during VRP, no ventricular activity can be sensed. (The atrial channel is also refractory during PVI.)

Figure 3B:
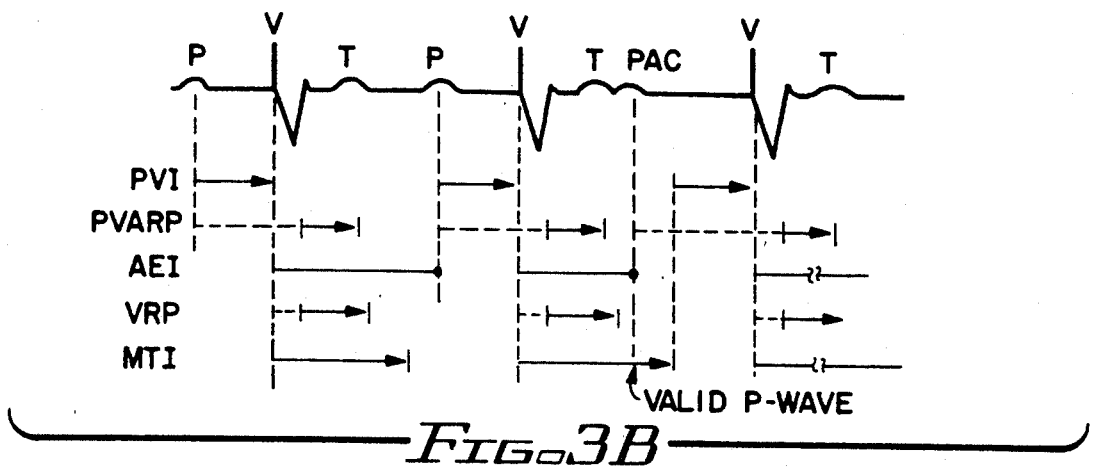
FIG. 3B is a similar composite timing diagram illustrating how A-V synchrony is maintained when only a ventricular stimulation pulse need be provided to the heart, and further illustrates one possible response of a pacemaker to a premature atrial contraction (PAC)

In FIG. 3B, a condition is depicted wherein a natural or sinus P-wave is present, and hence there is no need for the pacemaker to generate an A-pulse. When the sinus P-wave is sensed, the P-V interval, PVI, is initiated, and the pacemaker is alert in order to sense if an R-wave will occur. If an R-wave has not been sensed by the time the P-V interval times-out, then a V-pulse is generated as indicated. This V-pulse initiates the beginning of the atrial escape interval and PVARP. Prior to the termination of the AEI, a naturally-occurring P-wave is sensed, indicated by the dot on the AEI line. The sensing of the naturally-occurring P-wave inhibits the generation of an A-pulse, and initiates the beginning of a new P-V interval, at the conclusion of which another V-pulse is generated. This process continues for so long as the heart continues to generate sinus P-waves but fails to produce naturally-occurring R-waves.

FIG. 3B further illustrates one possible response of the pacemaker to a premature atrial contraction, or PAC. A premature atrial contraction is simply a contraction of the atrium that occurs prematurely or early in the normal A-V synchrony. The PAC shown in FIG. 3B occurs immediately subsequent to the second T-wave. The pacemaker responds to the PAC as though it were a sinus P-wave. That is, the occurrence of the PAC terminates the atrial escape interval. Further, when a P-wave occurs within MTI, as does the PAC shown in FIG. 3B, a latch circuit is set indicating that the sensed activity is considered a valid P-wave. The setting of this latch causes the P-V interval to be initiated at the end of the MTI. At the conclusion of this P-V interval, the V-pulse is generated. Once a V-pulse has been generated, the operation of the pacemaker continues in normal fashion.

Figure 3C:
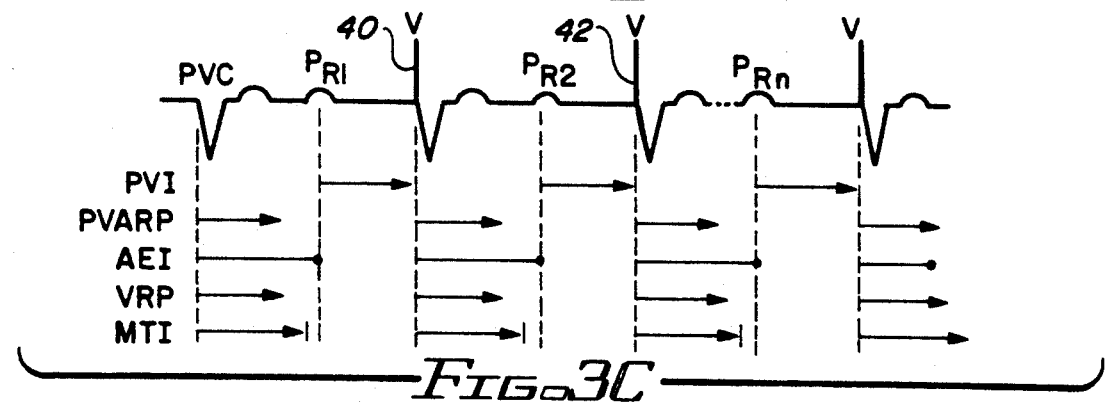
FIG. 3C is a composite timing diagram as in FIGS. 3A and 3B illustrating a PMT at a rate less than the maximum tracking rate (MTR) of the pacemaker.
Figure 3D:
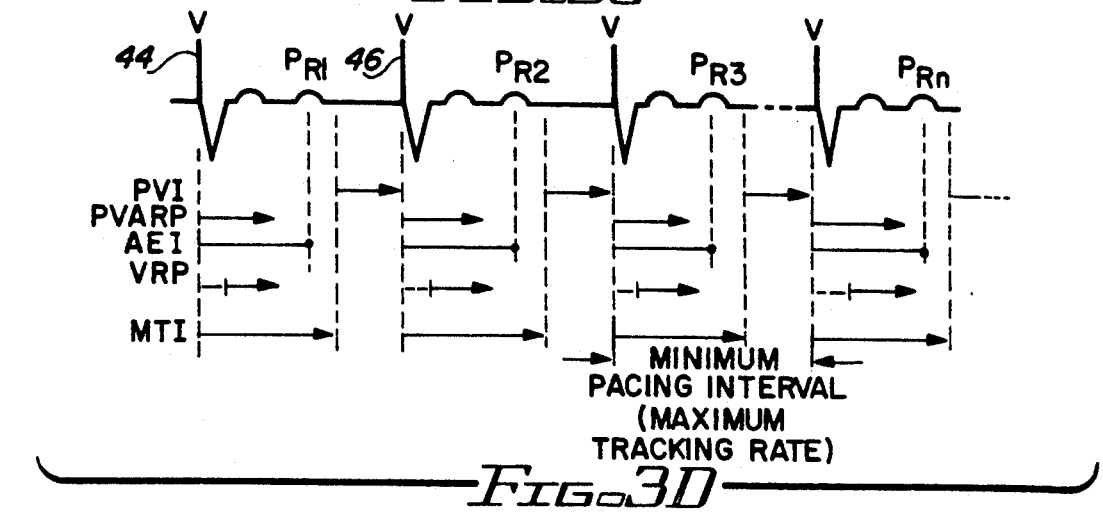
FIG. 3D is a composite timing diagram illustrating a PMT at the maximum tracking rate (MTR) of the pacemaker.

FIG. 3C is a composite timing diagram as in FIGS. 3A and 3B illustrating a PMT at a rate less than the maximum tracking rate (MTR) of the pacemaker. (The MTR of the pacemaker, as shown in FIG. 3D, is determined by the MTI plus the PVI.) A premature ventricular contraction, e.g., a PVC, triggers a first retrograde P-wave, $P_{R1}$, through retrograde condition as previously described. This retrograde P-wave is interpreted by the pacemaker sensing circuits as a normal P-wave. Thus, its occurrence triggers a P-V interval, PVI. At the conclusion of the PVI, a V-pulse 40 is generated. This V-pulse 40 causes the ventricles to contract, which contraction causes a second retrograde P-wave, $P_{R2}$, to occur. The second retrograde P-wave again triggers a P-V interval, PVI, at the conclusion of which a second V-pulse 42 is generated. The ventricular contraction caused by this second V-pulse 42 causes another retrograde P-wave, and the process repeats.

Note, as seen in FIG. 3C, that the time interval between a ventricular contraction and the occurrence of a retrograde P-wave, $P_R$, is longer than the minimum tracking interval, MTI. Hence, e.g., assuming the minimum tracking interval is 270 milliseconds, and the PVI is 130 milliseconds, the minimum pacing interval (MTI+PVI) is 400 milliseconds, corresponding to a maximum tracking rate (MTR) of approximately 150 beats per minute. However, because the P-V interval (controlled by the retrograde conduction time) is longer than the MTI, the overall pacing interval, and hence the PMT rate, is greater than 400 milliseconds, resulting in a PMT rate less than the MTR. For example, if the P-V interval is on the order of 310 milliseconds (some 40 milliseconds longer than the MTI), then the overall pacing interval is 440 milliseconds, corresponding to a PMT rate of about 136 bpm.

FIG. 3D shows a composite timing diagram illustrating a PMT condition wherein the PMT is constrained to operate at the maximum tracking rate (MTR). In FIG. 3D, it is assumed that this PMT condition is already established. Thus, a V-pulse 44 causes a first retrograde P-wave $P_{R1}$ to occur. This P-wave $P_{R1}$ occurs after the V-pulse 44 at a time that is subsequent to the termination of the PVARP (and hence at a time when the P-wave can be sensed), but is prior to the termination of the MTI. The programmed P-V interval, or PVI, cannot begin until the MTI times-out. In this regard, the retrograde P-wave $P_{R1}$ is similar to the PAC shown in FIG. 3B. After the termination of the maximum tracking interval MTI, the programmed P-V interval, PVI, begins, after which another V-pulse 46 is generated. A second retrograde P-wave $P_{R2}$ occurs prior to the termination of the next MTI, which MTI is triggered by the V-pulse 46. This process continues, with the retrograde P-wave always occurring prior to the termination of the MTI interval, the PVI not starting until the MTI times-out, and the V-pulse being generated at the conclusion of the pacemaker-defined PVI.

Figure 3E:
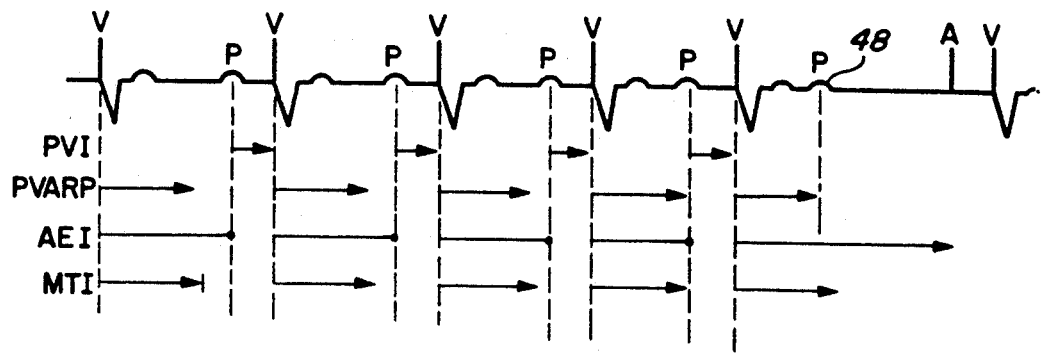
FIG. 3E is a composite timing diagram illustrating a sinus rate greater than the MTR of the pacemaker.

Referring next to FIG. 3E, a composite timing diagram illustrates an increasing sinus rate that ends up greater than the pacemaker-defined MTR. The sinus rate is initially sensed by the occurrence of P-waves that occur prior to the termination of the atrial escape interval, AEI, but after the termination of PVARP. The ventricle is stimulated with a V-pulse at the conclusion of the P-V interval (PVI), or programmed P-V delay, which interval or delay is triggered by the occurrence of a P-wave. The interval between the V-pulse and the subsequent P-wave, i.e., the V-P interval, gets progressively shorter until a P-wave 48 falls into PVARP. Once a P-wave falls into PVARP it is not sensed.

Figure 4A:
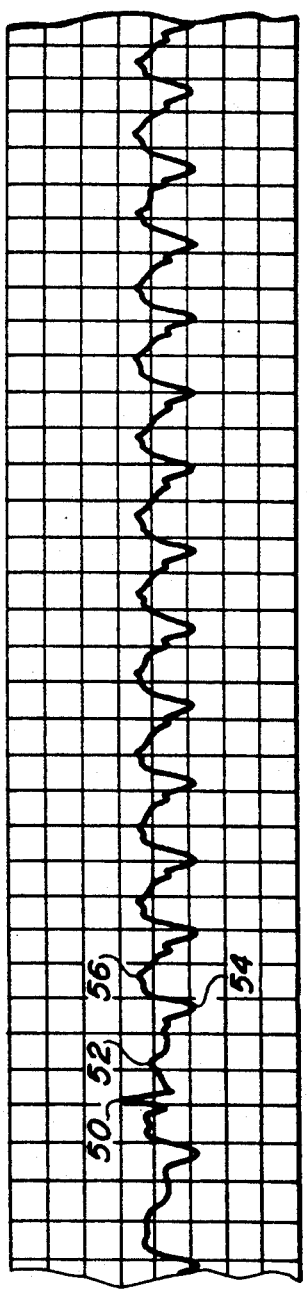
FIGS. 4A, 4B and 4C are actual ECG diagrams corresponding to the conditions shown in FIGS. 3C, 3D and 3E, respectively.
Figure 4B:
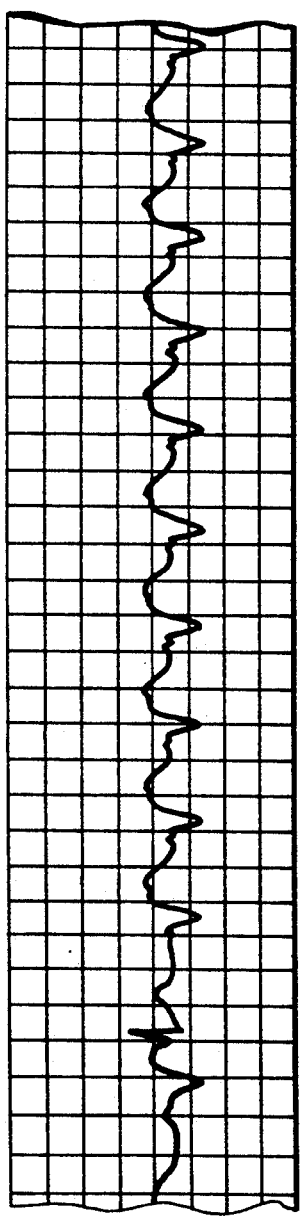
Figure 4C:
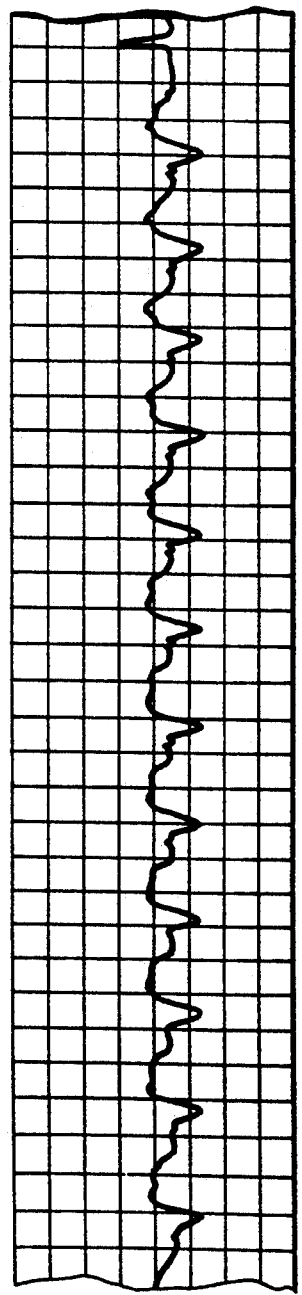

FIGS. 4A, 4B and 4C are representations of actual ECG diagrams that correspond, respectively, to the conditions schematically illustrated in FIGS. 3C, 3D and 3E. Each horizontal division in these ECG diagrams corresponds to 200 milliseconds. Each vertical division corresponds to some number of millivolts. In FIG. 4A, the maximum tracking rate is set to 150 beats per minute. Following a junctional beat 50, e.g. a PVC, there is a T-wave 52 with a retrograde P-wave superimposed thereon. Approximately 130 milliseconds later, the pacemaker paces the ventricle, causing a ventricular contraction, manifest by the inverted R-wave 54. This is followed by yet another retrograde P-wave 56. The PMT continues at approximately 136 bpm (every 440 milliseconds), which is less than the maximum tracking rate.

In FIG. 4B, an ECG representation of a PMT at 110 bpm is shown (545 milliseconds per cycle). The pacemaker is also programmed to have a maximum tracking rate of 110 bpm. Thus, in this case, even though a retrograde P-wave is sensed, the P-V interval (PVI) is not begun because the MTI has not yet timed-out. Therefore, when the MTI times-out, the P-V interval begins, and a V-pulse is generated upon the timing out of the PVI. Thus, in FIG. 4B, the PMT occurs at the programmed maximum tracking rate of 110 bpm.

In FIG. 4C, the sinus rate manifest by the ECG is faster than the maximum tracking rate. In this case, the V-to-P interval, or "V-P interval," progressively decreases until a P-wave falls into the PVARP and is not sensed. This is not a PMT.

Figure 5A:
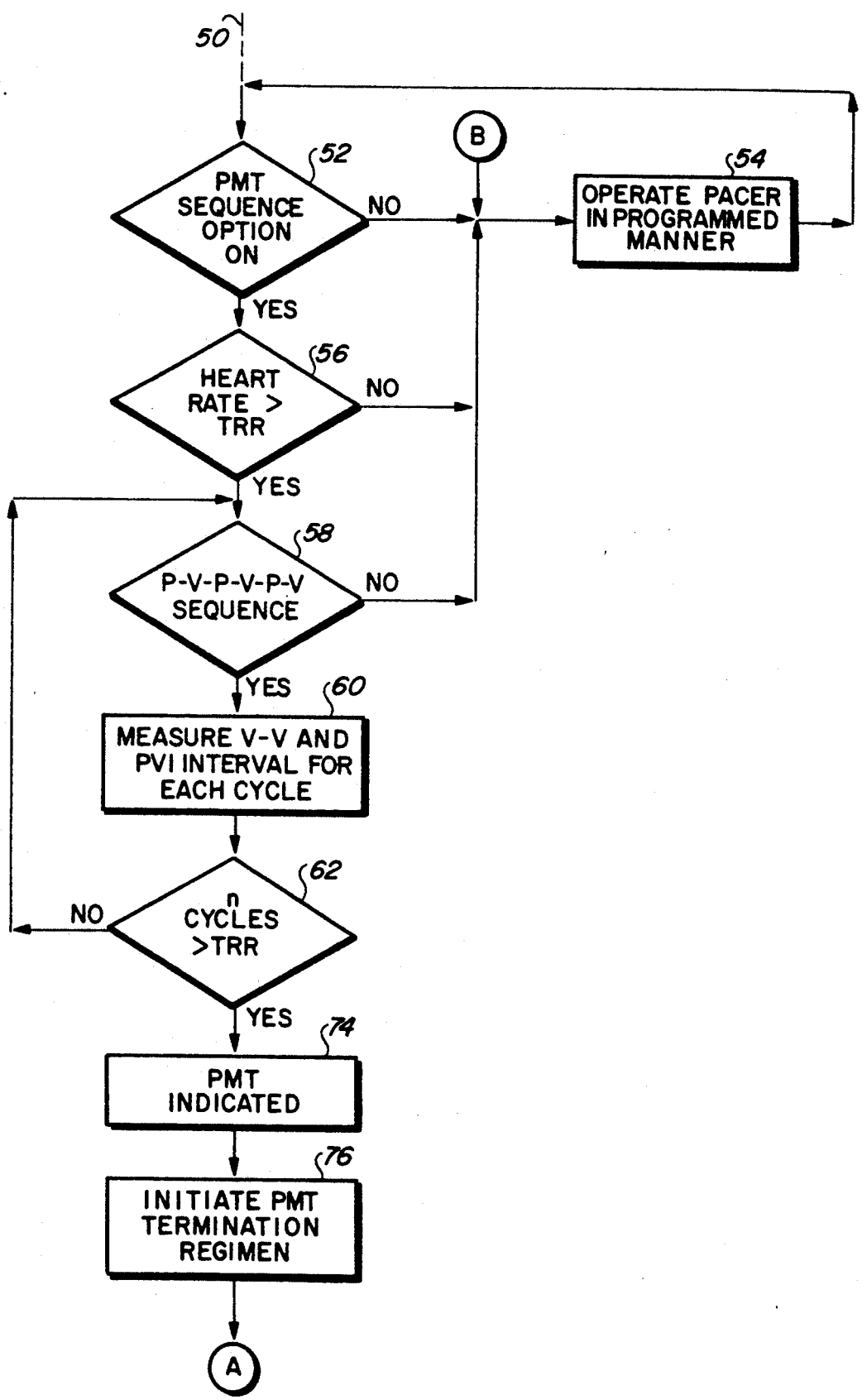
FIGS. 5A and 5B are flowcharts illustrating one embodiment of the PMT response and termination method of the present invention.

Referring to FIG. 5A, there is shown a flowchart illustrating the operation of one embodiment of the PMT termination method of the present invention. In this flowchart, and as in the other flowcharts described herein, the various steps of the PMT response method are summarized in individual "blocks" or boxes. Such blocks or boxes describe specific actions or decisions that must be made or carried out as the PMT response method proceeds. Specific circuitry that carries out these steps can readily be fashioned by those skilled in the art. Particularly, where a microprocessor, or equivalent programmed controlled device, is employed as a key element of the pacemaker, i.e., where the control logic 12 (FIG. 2) includes a microprocessor, the flowcharts presented herein provide the basis for a "control program" that may be used by such microprocessor, or equivalent, to effectuate the desired control of the pacemaker. Such control program may be stored in ROM (read only memory), RAM (random access memory), or other memory 30 (FIG. 2) associated with the control logic 12. Those skilled in the programming and pacemaker arts may readily write such a control program based on the flowcharts and other descriptions presented herein.

As shown in FIG. 5A, the flowchart begins with a dashed line 50. This dashed line 50 schematically emphasizes or represents that the program included within the flowchart of FIG. 5A typically forms part of an overall control program used in conjunction with and as a control function for the pacemaker.

A first step of the PMT response method shown in FIG. 5A involves determining whether the PMT response option is turned ON, as depicted in block 52. If the option is not turned ON, then the pacemaker (or "pacer") continues to operate in conventional manner according to its then-existing programmed control parameters, as indicated in block 54. If the PMT response option is turned ON, then a determination is made as to whether the heart rate exceeds a reference rate, referred to as the tachycardia reference rate, or TRR (block 56). Preferably the TRR is about 100 bpm. A heart rate above the TRR may be indicative of a tachycardia condition. Any suitable rate determination technique may be used for this purpose. Typically, the heart rate is determined by measuring the interval between succeeding R-waves (whether resulting from a natural or paced contraction).

Continuing with the method shown in FIG. 5A, if the heart rate exceeds the TRR value, then a determination is made as to whether the particular sequence associated with a PMT is present, as shown in block 58. For a PMT, this sequence includes a tracked P-wave followed by a V-pulse for each successive cardiac cycle. (Stated another way, every V-pulse must be preceded by a P-wave.) Hence, only if the monitored cardiac cycles include this P-wave and V-pulse, P-wave and V-pulse sequence, then a PMT may be indicated. If this sequence is not present, then the rapid heart rate condition, determined at block 56, is not a PMT, and the PMT recognition method terminates by returning to operate the pacer in its normal programmed manner (block 54). The rapid heart rate condition may derive from a sensor-indicated rate.

If the proper cardiac sequence is detected at block 58, then n cycles of the sequence are monitored in order to measure the V-to-V interval (V-V interval) of each cycle, as shown at block 60. If at any time during the monitoring of these n cycles, the proper sequence does not continue, or the heart rate (measured by V-V interval, for example) falls below the TRR value, then the PMT detection method terminates. The number of cardiac cycles thus monitored, i.e., the value of n for this embodiment of the invention, is preferably about 10 cardiac cycles. However, it may be any value, e.g., 2-20, which value may be programmably set to a desired value. The PVI interval is also measured (block 60) during the PMT recognition method in order to be used later during the PMT termination method.

Accordingly, an appropriate PMT termination regimen, such as described in this invention, is initiated for one cardiac cycle (block 76). After invoking the PMT termination regimen, the pacemaker operates in its programmed manner (block 54). If the PMT continues, i.e., if the PMT termination regimen was not successful in terminating the PMT, then the PMT recognition process repeats with a subsequent PMT response after the completion of n V-V cycles (typically 128 V-V cycles).

Figure 5B:
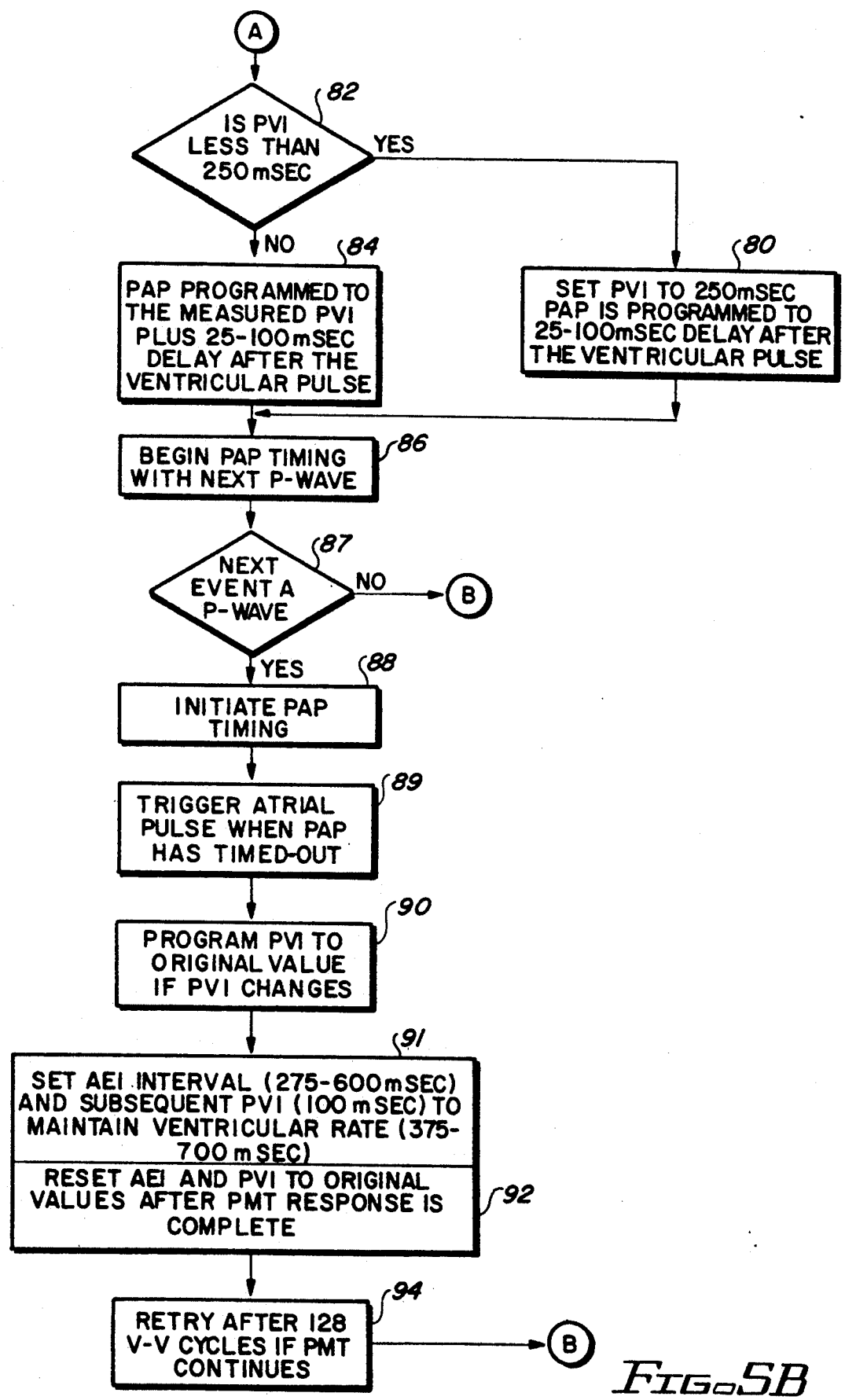

FIG. 5B shows the PMT termination regimen as identified in FIG. 5A, block 76, for the preferred embodiment. After a PMT has been detected, then block 82 in FIG. 5B, determines if the previously measured PVI is less than 250 milliseconds. If PVI is less than 250 milliseconds, the YES path is taken and block 80 is invoked (which corresponds to the waveforms of FIG. 7). If, on the other hand, PVI is not less than 250 milliseconds, the NO path is taken and block 84 is invoked (which corresponds to the waveforms of FIG. 6).

The NO condition, or the condition shown in FIG. 6, will be discussed first. In block 84, the PAP is adjusted to be 25-100 milliseconds longer than the measured PVI. This is done at the beginning of the third cycle of FIG. 6. In block 86 and 87, the next sensed signal must be a retrograde P-wave to qualify the heart rate as a PMT; if not, then the processing returns to block 54 of FIG. 5A. If a retrograde P-wave is detected, then this commences the PAP timing in block 88. Block 89 is the time-out of the PAP timing wherein the timed atrial pulse is generated. If the PVI changes from the previous value, then PVI is programmed to its original value (block 90). The AEI (block 91) and subsequent PVI intervals (block 92) are then adjusted during the fourth cycle of FIG. 6 in order to maintain the V-V rate at the rate measured during the second cycle of FIG. 6 and to allow for at least 250 milliseconds minimum time interval between the PAP atrial pulse and the AEI atrial pulse. This time interval allows for the delivery of an effective AEI atrial pulse. In block 94, 128 V-V cycles are counted before repeating the PMT regimen. Subsequent to repeating a PMT termination sequence, processing returns to block 54 in FIG. 5A to resume normal pacer operation.

Upon the occurrence of the YES condition in block 82, processing goes to block 80 which temporarily programs the PVI interval to 250 milliseconds and the PAP timing to be 25 to 100 milliseconds longer than the 250 milliseconds PVI. The PVI interval is programmed back to its original value in block 90. Obviously when the NO path is taken from block 82, no change is made in the PVI by block 106.

Figure 6:
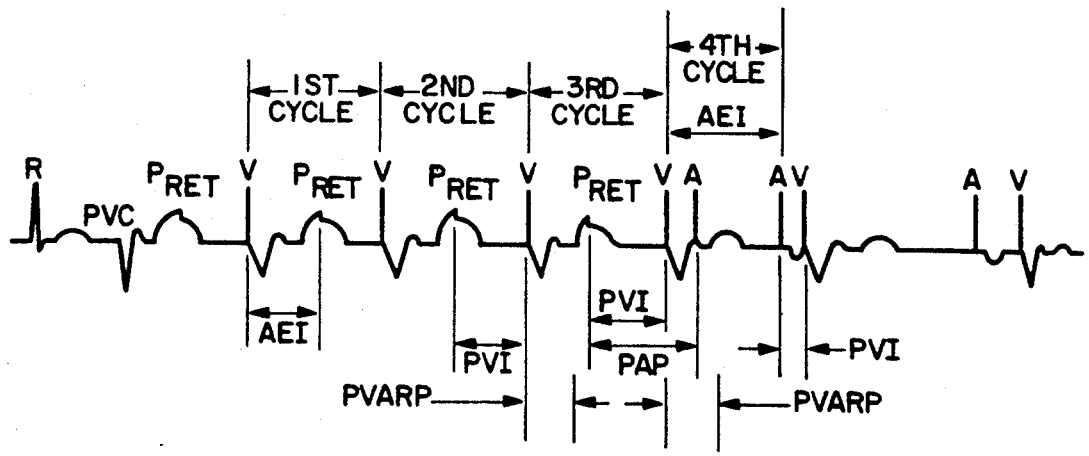
FIG. 6 is a composite timing diagram showing the termination of a PMT in accordance with the method shown in FIGS. 5A and 5B when the PMT is at the maximum tracking rate.
Figure 7:
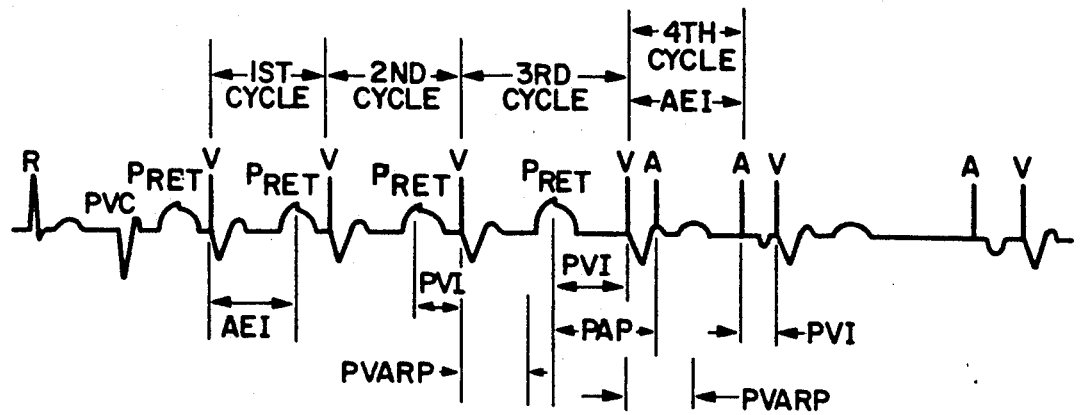
FIG. 7 is a composite timing diagram showing the termination of a PMT in accordance with the method of FIGS. 5A and 5B when the PMT is below the maximum tracking rate.

Operation of the PMT termination method shown in FIG. 5A and 5B are illustrated by the composite timing diagrams of FIGS. 6 and 7. FIG. 6 illustrates a PMT condition at the maximum tracking rate, and FIG. 7 illustrates a PMT condition below the maximum tracking rate. For both FIGS. 6 and 7 it is assumed that a fast tachycardia condition exists containing the proper sequence of P-waves and V-pulses. That is, the requirements imposed by blocks 56, 58 and 62 of the flowchart of FIG. 5A have been satisfied.

FIG. 6 shows a PMT that was initiated by a PVC and the pacemaker is tracking retrograde P-waves (Pret) at the maximum tracking rate. This accounts for the long PVI which is caused by the maintenance of the V-V interval at the maximum tracking rate. During the third V-V cycle, the PMT termination sequence is initiated and is terminated at the completion of the fourth V-V interval. If the PVI, which was previously measured during the PMT (for example during the second V-V cycle), was determined to be greater than 200-250 milliseconds as a result of the pacemaker operating at the maximum tracking rate, then the PAP interval is programmed to be 25-100 milliseconds longer than the measured PVI. It should be noted that the PVI interval during a PMT is very stable in time and will not change very much from cycle to cycle. The resulting timed atrial pulse is timed to occur 25-100 milliseconds after the ventricular stimulus. During both the ventricular and atrial pulses, pacemaker refractories are activated so as to avoid sensing afterpotentials which result from the pacemaker pulses. The antegrade and retrograde conduction paths will collide and be extinguished with the appropriately timed atrial pulse. The PAP time (greater than 250 milliseconds) is chosen to allow the resulting atrial pulse to be effective and also to prevent stimulating the atrium during the vulnerable period, which stimulation may induce an arrhythmia or not cause depolarization because of refractory tissue in the atrium.

The PAP time should be a minimum of 25 milliseconds longer than the measured PVI and is programmable up to 100 milliseconds longer than the measured PVI. This ensures that the atrial pulse will occur after the ventricular pulse and during atrial and ventricular refractory periods (PVARP and VRP). The AEI is programmed in the DDD modality to allow for the AEI atrial pulse to be effective (the second atrial pulse at the end of the fourth cycle of FIG. 6).

The time (AEI) between the ventricular pulse and the AEI atrial pulse is programmable from 275-600 milliseconds. This AEI time is adjusted to maintain a ventricular rate at or near an exercise or PMT ventricular rate level and to keep the atrium refractory and thus prevent the continuation of the PMT. Depending on the programing of PVARP and AEI, the alert time for sinus P-waves would be the time from the end of PVARP to the AEI atrial pulse. If a sinus P-wave is detected after PVARP, then the pacemaker tracks this P-wave, initiating a PVI, and issues a corresponding ventricular pulse. Any P-wave occurring after PVARP is considered a valid P-wave and not retrograde conduction since the PAP atrial pulse has caused the atrium to depolarize and to become refractory to the retrograde P-wave. This allows for shorter PVARP intervals during the PMT sequence and, in most cases, PVARP does not have to be programmed at all since the PAP time does not allow an atrial pulse to occur more than 100 milliseconds after the beginning of PVARP and VRP refractories.

PVARP may require extension if the PAP atrial pulse is near the end of a short PVARP interval (less than 100 milliseconds from the end of PVARP). This is only necessary to prevent afterpotential detection after the atrial pacer pulse and not to prevent retrograde P-wave detection. PVARP advantageously is not required to be extended to mask retrograde conduction (490 milliseconds in one embodiment), thus having the advantage of not slowing down the ventricular rate during the PMT sequence (due to a long programmed PVARP and subsequent alert interval) or failing to sense true sinus P-waves occurring during an extended PVARP. The ventricular rate can be maintained or slowed down only a small amount during a PMT sequence, which can occur during physical activity.

As shown in FIG. 6, the V-V rate is maintained near the maximum tracking rate during the PMT sequence (fourth cycle). After the PMT sequence has terminated the PMT, normal A-V pacing continues at a rate which may be based on either a sensor-indicated rate or the programmed minimum rate. Also, in order to help maintain an appropriate V-V rate, the PVI can be shortened following the PMT sequence, since AEI+PVI=V-V INTERVAL. The PMT sequence occurs only once with each PMT detection. A period of time (for example, 128 V-V cycles) is required to elapse in order to invoke another PMT sequence again so as to prevent repetitiously invoking the PMT sequence. This might occur during a PMT detection of normal sinus tachycardia and responding with a PMT sequence which, of course, would be inappropriate during sinus tachycardia.

FIG. 7 is similar to FIG. 6, except that the measured PVI is less than 200–250 milliseconds. The PMT is below the maximum tracking rate which usually indicates that the PVI will be less than 200 milliseconds. In order to maintain a 250–350 milliseconds delay from the retrograde P-wave to the PAP atrial pulse (which time will allow the PAP atrial pulse to be effective and also not compete with the previous retrograde P-wave), the PVI is temporarily programmed longer during the PAP atrial pulse response. The result is to slow the ventricular rate down slightly, but it is necessary in order for the PAP atrial pulse not to compete with the retrograde P-wave that initiated the PAP interval. For example, if the measure PVI was 100 milliseconds, the PVI during the third cycle is temporarily programmed to 250 milliseconds which would allow the PAP atrial pulse to occur at 275–350 milliseconds after the retrograde P-wave. The PAP atrial pulse will depolarize the atrium with subsequent refractory time and thus prevent a subsequent retrograde P-wave from occurring.

The PVI is then returned to its original value (100 milliseconds in the previous example) at the beginning of the fourth cycle in preparation for subsequent P-wave activity. As can be seen, the third V-V cycle is at a slower rate than the previous cycle in order to allow for an appropriate PAP time.

The pacing rate slowdown at rates below the maximum tracking rate is not as critical as compared to rates at the maximum tracking rate, because a V-V rate slowdown of 150 milliseconds (250 milliseconds temporary programmed PVI minus the measured PVI of 100 milliseconds) is not a significant drop in pacing rate. For example, if the V-V rate of a PMT below the maximum tracking rate was 100 beats per minute or 600-millisecond interval, then a slowdown of 750 milliseconds would be 80 bpm or a drop of 20 bpm for one cycle. This drop in pacing rate can be further reduced by temporarily programming the PVI to 175 milliseconds and programming the PAP time to 100 milliseconds after the PVI during the PMT sequence. Accordingly, a PAP time from the retrograde P-wave to the PAP atrial pulse of 275 milliseconds results and a rate reduction to only 89 bpm. Thus, by programming the temporary PVI and the PAP interval, the rate slowdown during the third cycle can be minimized and thus maintain a PAP time of greater than 250 milliseconds in order to allow for an effective PAP atrial pulse. The AEI and PVI times during the fourth cycle can also be programmed to maintain V-V rate, as previously described for FIG. 6.

Figure 8:
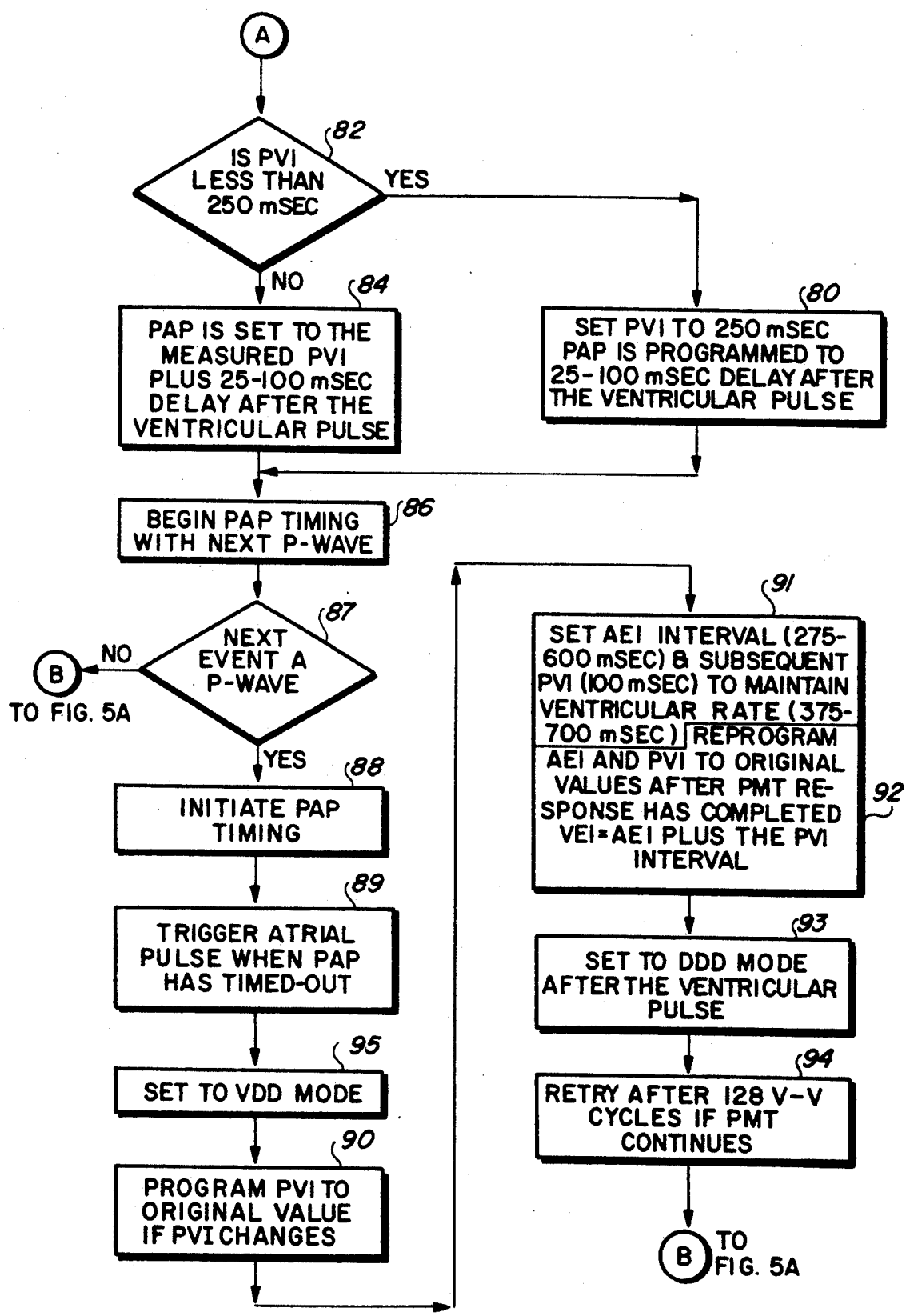
FIG. 8 is a flowchart illustrating another embodiment of the PMT response and termination method of the present invention.

Referring next to FIG. 8, a flowchart illustrating the operation of another embodiment of the PMT termination system and method thereof is shown. The processing shown in FIG. 8 is similar to that shown in FIG. 5B, except that the pacing mode changed from the DDD to the VDD modality during the PMT sequence after the PAP atrial pulse. Furthermore, the sequence now relies on VEI timing rather than on AEI timing. The time between a ventricular pulse and the following VEI ventricular pulse is programmable from 375–700 milliseconds. Depending upon the programming of PVARP and VEI, the alert time for sinus P-waves would be the time from the end of PVARP to the VEI ventricular pulse. If a sinus P-wave is detected after the PAP atrial pulse, the pacemaker will track this P-wave, thereby initiating a PVI and subsequent ventricular pulse. The VEI is changed by programming the AEI and PVI in the VDD mode. The method of this embodiment has the advantage of maintaining the V-V interval at very high PMT rates since there is no AEI atrial pulse and the VEI pulse in the fourth cycle is programmable to 375 milliseconds or 160 bpm, if desired. This processing may be used during very high PMT rates or high levels of activity during which the V-V interval is to be maintained. The embodiment has the advantage of not producing a second atrial pulse which must be timed so as not to compete with the PAP atrial pulse. This gives even more flexibility in programming the V-V interval time during the PMT sequence.

Processing in accordance with the flowchart of FIG. 8 is similar to that of FIGS. 5A and 5B, and therefore, identification of the various blocks, with identical functions in both FIGS. 5 and 8, remains the same. As discussed in detail above however, setting the pacing modality to VDD is performed in block 95 and setting the pacing modality to DDD is performed in block 93.

Referring now to FIG. 9, the composite timing diagram illustrates functioning of the system during operation at the maximum tracking rate. The distinction between the operation described for and shown in FIG. 6 is that the VEI is used rather than the AEI. The VEI may be programmed based upon the value of selectively defined intervals, and preferably, is set equal to the AEI plus the PVI. For the above conditions, the time to the atrial pulse from the retrograde P-wave is from about 25–100 milliseconds greater than the PVI. The AEI may be in the range of 275–600 milliseconds so that in such case, the VEI may have a maximum value of about 700 milliseconds. The AEI and PVI times are adjusted to maintain a ventricular rate at or near the exercise rate or the PMT ventricular rate level.

For the condition, as shown in FIG. 10, where the pacemaker is tracking retrograde P-waves below the maximum tracking rate, the PVI is temporarily set to 250 milliseconds and the time to the atrial pulse from the retrograde P-wave is from about 25–100 milliseconds longer than the PVI. Furthermore, after the delivery of the timed atrial pulse, operation of the pacemaker goes to the VDD mode and immediately after the first ventricular pulse following the timed atrial pulse, the pacemaker returns to the DDD mode of operation.

Although FIGS. 6–10 show four cycles, where the V-V interval is measured in the first and second cycles and PVI is measured in the second cycle, it is to be understood that the order of measuring these values may be changed, i.e., PVI measured in the first cycle and the V-V interval measured in the second cycle, to obtain equivalent results. Moreover, both values may be sensed or determined in the same cycle, for example, in the second cycle, and thereby eliminating the first cycle.

Additionally, the V-V interval is measured to determine whether the heart rate exceeds the TRR. Although not mandatory, it is advantageous to measure the V-V interval over several cycles, preferably 2-20, in order to confirm the heart rate above the TRR.

While the invention has been described by means of specific embodiments in applications thereof, it is understood that numerous modifications and variations could be made thereto by those skilled in the art without departing from the spirit and scope of the invention. It is therefore to be understood that within the scope of the following claims, the invention may be practiced otherwise than as specifically described herein.

I claim:

1. An implantable pacemaker including means for terminating a pacemaker-mediated tachycardia (PMT) comprising:
   detection means within said implantable pacemaker for detecting heart rate and for detecting P-waves and V-pulses and for detecting a prescribed sequence of cardiac cycles, each cardiac cycle of said prescribed sequence comprising a P-wave followed by a V-pulse, the time interval between said P-wave and said V-pulse of each cardiac cycle comprising a P-V interval (PVI), a time interval between successive V-pulses comprising a V-V interval, the detection means further comprising means for timing a timed atrial pulse from a detected P-wave occurring in a corresponding one of the cycles in the sequence of cardiac cycles; and
   stimulation means responsive to the detection means for stimulating the atrium by said timed atrial pulse for terminating a PMT.

2. The pacemaker of claim 1, wherein the stimulation means includes means for stimulating the atrium after the heart rate exceeds a prescribed rate.

3. The pacemaker of claim 2, wherein the stimulation includes means for stimulating the atrium after a P-wave followed by a V-pulse occurs successively in the sequence of cardiac cycles.

4. The pacemaker of claim 3, wherein the stimulation means includes means for stimulating the atrium after the occurrence of a prescribed number of successive V-V intervals in the sequence of cardiac cycles.

5. The pacemaker of claim 4, wherein the stimulation means includes means for stimulating the atrium with a timed atrial pulse when the PVI exceeds a prescribed amount.

6. The pacemaker of claim 5, wherein the timing means times the timed atrial pulse, a prescribed delay from said P-wave.

7. The pacemaker of claim 6, wherein the prescribed delay comprises the PVI plus a delay interval, such delay interval comprising a range of about 25-100 milliseconds.

8. The pacemaker of claim 7, wherein the prescribed amount comprises approximately 250 milliseconds.

9. The pacemaker of claim 7, wherein the implantable pacemaker further comprises means for providing an atrial escape interval (AEI), the AEI comprising the interval from a V-pulse to the following atrial pulse, wherein the AEI comprises a time interval ranging from 275-600 milliseconds, and wherein the PVI comprises approximately 100 milliseconds, for maintaining a corresponding ventricular pulsing rate.

10. The pacemaker of claim 9 wherein the stimulation means includes means for stimulating the atrium by a timed atrial pulse upon the occurrence of a prescribed number of V-V intervals.

11. The pacemaker of claim 10, wherein the prescribed number of V-V intervals comprises about 128.

12. The pacemaker of claim 1, wherein the P-wave detected by said detecting means comprises a retrograde P-wave.

13. An implantable pacemaker for terminating a pacemaker-mediated tachycardia (PMT) in a patient comprising:
    detection means within the implantable pacemaker for detecting P-waves and V-pulses, the P-waves including retrograde P-waves, and for detecting a prescribed sequence of cardiac cycles, each cardiac cycle of the prescribed sequence comprising a P-wave followed by a V-pulse, the time interval between the P-wave and the V-pulse of each cardiac cycle comprising a P-V interval (PVI), said PVI also being adjustable to at least an original value and a prescribed value, the time interval between successive V-pulses comprising a V-V interval, said detection means further comprising means for timing a timed atrial pulse from a detected retrograde P-wave occurring in the sequence of cardiac cycles;
    means for determining the duration of the PVI and for adjusting the PVI to the prescribed value when the PVI is less than the prescribed value; and
    stimulation means responsive to the detection means for stimulating the atrium by said timed atrial pulse for terminating a PMT.

14. The pacemaker of claim 13, wherein the prescribed value comprises approximately 250 milliseconds.

15. The pacemaker of claim 13, wherein the timing means times the timed atrial pulse a prescribed delay from said retrograde P-wave.

16. The pacemaker of claim 15, wherein the prescribed delay comprises the PVI plus a delay interval, such delay interval comprising a range of about 25-100 milliseconds.

17. The pacemaker of claim 16 including means for retaining prior PVI values; means for comparing consecutive PVI values to detect a change thereof; and means for adjusting the PVI to the original value when such change is detected.

18. The pacemaker of claim 16, wherein the implantable pacemaker includes the DDD and VDD modes of operation, the pacemaker further comprising means for pacing in the VDD mode at least immediately after the occurrence of the timed atrial pulse, and for pacing in the DDD mode upon the occurrence of a V-pulse immediately subsequent to the timed atrial pulse.

19. An implantable pacemaker for terminating a pacemaker-mediated tachycardia (PMT) in a patient, wherein the pacemaker includes DDD and VDD modes of operation, the pacemaker comprising:
    detection means within the implantable pacemaker for detecting P-waves and V-pulses, the P-waves including retrograde P-waves and for detecting a prescribed sequence of cardiac cycles, each cardiac cycle of the prescribed sequence comprising a P-wave followed by a V-pulse, the time interval between the P-wave and the V-pulse of each cardiac cycle comprising a P-V interval (PVI), the time interval between successive V-pulses comprising a V-V interval, the time interval between successive V-V pulses with an A-pulse therebetween comprising a VEI interval, the time interval between a V-pulse and the following retrograde P-wave comprising an atrial escape interval (AEI);

the prescribed sequence of cardiac cycles includes at least four cycles comprising a first, a second, a third and a fourth cycle, the four cycles occurring successively, wherein the detection means measures the V-V interval in the first and second cycles for comparison to a tachycardia recognition rate (TRR), and further measures the PVI in the second cycle for comparison to a prescribed value; and stimulation means responsive to the detection means for stimulating the atrium by said timed atrial pulse, for terminating a PMT.

20. The pacemaker of claim 19, including means for timing the timed atrial pulse from a retrograde P-wave detected in the third cycle and wherein the time to the timed atrial pulse comprises the PVI plus a delay interval, such delay interval being in the range of about 25-100 milliseconds, and wherein the stimulation means stimulates the atrium by a timed atrial pulse occurring in the fourth cycle.

21. The pacemaker of claim 20, further comprising means for adjusting the AEI and the PVI, wherein the adjusting means adjusts the AEI in the fourth cycle in the range of approximately 275-600 milliseconds, and the PVI to approximately 100 milliseconds for maintaining the V-V interval in the range of about 275-700 milliseconds.

22. The pacemaker of claim 19 further comprising means for adjusting the PVI in the third cycle to a prescribed value when the PVI is less than the prescribed value, such prescribed value comprising approximately 250 milliseconds.

23. The pacemaker of claim 22, including means for pacing in the VDD mode immediately subsequent to the timed atrial pulse.

24. The pacemaker of claim 23, including means for pacing in the DDD mode upon termination of the fourth cycle.

25. An implantable pacemaker for terminating a pacemaker-mediated tachycardia (PMT) in a patient comprising:

detection means within the implantable pacemaker for detecting P-waves and V-pulses, the P-waves including retrograde P-waves, and for detecting a prescribed sequence of cardiac cycles, each cardiac cycle of the prescribed sequence comprising a P-wave followed by a V-pulse, the time interval between the P-wave and the V-pulse of each cardiac cycle comprising a P-V interval (PVI), the time interval between successive V-pulses comprising a V-V interval, the time interval between successive V-V pulses with an A-pulse therebetween comprising a VEI interval, the time interval between a V-pulse and the following retrograde P-wave comprising an atrial escape interval (AEI), the detection means further comprising means for timing a timed atrial pulse from a detected retrograde P-wave occurring in the sequence of cardiac cycles and for detecting the value of the AEI and the PVI in one cycle of the sequence of cardiac cycles and for timing a timed atrial pulse from a retrograde P-wave occurring in another one of the cycles in the sequence, and stimulation means responsive to the detection means for stimulating the atrium by said timed atrial pulse in still another one of the cycles in the sequence for terminating a PMT.

26. A method for terminating a PMT in a patient having an implanted pacemaker, said method comprising the steps of:

(a) sensing a V-pulse followed by a P-wave in a plurality of successive cardiac cycles to thereby sense an atrial escape interval AEI;

(b) sensing a P-wave followed by a V-pulse in a plurality of successive cardiac cycles to thereby sense a PVI;

(c) sensing a first V-pulse followed by a second V-pulse in a plurality of successive cardiac cycles to thereby sense a V-V interval, the V-V interval comprising the elapsed time between the first V-pulse and the second V-pulse;

(d) sensing if the plurality of successive cardiac cycles sensed in step (c) occurs at a rate in excess of a tachycardia reference rate (TRR);

(e) sensing if the sequence of a P-wave followed by a V-pulse sensed in step (b) or a V-pulse followed by a P-wave sensed in step (a) continues repetitiously for a prescribed number of sequences;

(f) sensing if the number of V-V intervals exceeds a prescribed number wherein the rate sensed in step (d) exceeds the TRR and wherein the sequence of P-waves and V-pulses sensed in step (e) continues repetitiously;

(g) sensing if the PVI is less than a prescribed value and adjusting the PVI to the prescribed value when the PVI is less than the prescribed value;

(h) stimulating the atrium with an atrial pulse timed from a P-wave, a prescribed delay, the delay comprising the PVI of step (g) plus a delay interval, the delay interval comprising a range of approximately 25-100 milliseconds.

27. The method of terminating a PMT in a patient, as set forth in claim 26, further comprising the steps of:

(i) adjusting the AEI in the range of about 275-600 milliseconds; and (j) adjusting the PVI to about 100 milliseconds for maintaining the V-V interval in the range of about 375-700 milliseconds.

28. The method of terminating a PMT in a patient, as set forth in claim 27, further comprising the step of:

(k) indicating the termination of a PMT when either the ventricular rate determined from the V-V interval falls below a tachycardia reference rate or the P-wave followed by a V-pulse sequence has terminated or a V-pulse followed by a P-wave sequence has terminated.

29. The method of terminating a PMT in a patient, as set forth in claim 28, further comprising the steps of repeating the steps (a)-(k) when termination of a PMT is not indicated in step (k).

30. The method of terminating a PMT in a patient, as set forth in claim 29, further comprising the step of:

(l) counting a prescribed number of V-V intervals prior to repeating steps (a)-(k).

31. The method of terminating a PMT in a patient, as set forth in claim 30, wherein the prescribed number comprises about 128.

32. The method of terminating a PMT in a patient, as set forth in claim 26, wherein the prescribed value of step (g) comprises about 250 milliseconds.

33. The method of terminating a PMT in a patient, as set forth in claim 26, wherein the implanted pacemaker includes the VDD mode of operation, the method further comprising the step of:

(n) commencing the VDD mode of operation immediately after the timed atrial pulse of step (h).

34. The method of terminating a PMT in a patient, as set forth in claim 26, wherein the implanted pacemaker includes the DDD mode of operation, the method further comprising the step of commencing the DDD mode of operation upon the occurrence of the V-pulse immediately following the timed atrial pulse of step (h).

35. An implantable pacemaker including means for terminating a pacemaker-mediated tachycardia (PMT) comprising:

detection means within said implantable pacemaker for detecting heart rate and for detecting P-waves and V-pulses and for detecting a prescribed sequence of cardiac cycles, each cardiac cycle of said prescribed sequence comprising a P-wave followed by a V-pulse, the time interval between said P-wave and said V-pulse of each cardiac cycle comprising a P-V interval (PVI), a time interval between successive V-pulses comprising a V-V interval, the detection means further comprises means for timing a timed atrial pulse from a detected P-wave occurring in a corresponding one of the cycles in the sequence of cardiac cycles; and stimulation means responsive to the detection means for stimulating the atrium by said timed atrial pulse for terminating a PMT when the heart rate exceeds approximately 100 pulses per minute.

36. An implantable pacemaker including means for terminating a pacemaker-mediated tachycardia (PMT) comprising:

detection means within said implantable pacemaker for detecting heart rate and for detecting P-waves and V-pulses and for detecting a prescribed sequence of cardiac cycles, each cardiac cycle of said prescribed sequence comprising a P-wave followed by a V-pulse, the time interval between said P-wave and said V-pulse of each cardiac cycle comprising a P-V interval (PVI), a time interval between successive V-pulses comprising a V-V interval, the detection means further comprises means for timing a timed atrial pulse from a detected P-wave occurring in a corresponding one of the cycles in the sequence of cardiac cycles; and stimulation means responsive to the detection means for stimulating the atrium by said timed atrial pulse for terminating a PMT when the number of successive V-V intervals in the sequence of cardiac cycles comprises a number ranging from 2-20.

37. An implantable pacemaker for terminating a pacemaker-mediated tachycardia (PMT) in a patient comprising:

detection means within the implantable pacemaker for detecting P-waves and V-pulses, the P-waves including retrograde P-waves, and for detecting a prescribed sequence of cardiac cycles, each cardiac cycle of the prescribed sequence comprising a P-wave followed by a V-pulse, the time interval between the P-wave and the V-pulse of each cardiac cycle comprising a P-V interval (PVI), said PVI also being adjustable to at least a first prescribed value and a second prescribed value, the time interval between successive V-pulses comprising a V-V interval;

means for timing a timed atrial pulse a prescribed delay from a detected P-wave occurring in the sequence of cardiac cycles;

means for determining the duration of the PVI and for adjusting the PVI to the first prescribed value when the PVI is less than the first prescribed value; and stimulation means responsive to the detection means for stimulating the atrium by atrial pulses, such atrial pulses comprising at least said timed atrial pulse, the time interval between a V-pulse followed by the atrial pulse which immediately follows the timed atrial pulse comprising an atrial escape interval (AEI), said AEI also being adjustable to a third prescribed value, and means for adjusting the PVI to the second prescribed value and for adjusting the AEI to the third prescribed value for maintaining the V-V interval.

38. The pacemaker of claim 37, wherein the P-wave detected by said detecting means is a retrograde P-wave.

39. The pacemaker of claim 37, wherein the first prescribed value comprises approximately 250 milliseconds.

40. The pacemaker of claim 37, wherein the second prescribed value comprises approximately 100 milliseconds.

41. The pacemaker of claim 37, wherein the third prescribed value comprises a range of about 275-600 milliseconds.

42. The pacemaker of claim 37, wherein the prescribed delay comprises the PVI plus a delay interval, such delay interval comprising a range of about 25-100 milliseconds.

* * * * *